US012575766B1

(12) United States Patent

Reynard

(10) Patent No.: US 12,575,766 B1
(45) Date of Patent: Mar. 17, 2026

(54) AI-ASSISTED RAMAN SPECTROSCOPY SYSTEM FOR BIOMARKER ANALYSIS OF AQUEOUS HUMOR

(71) Applicant: Michael Reynard, Santa Monica, CA (US)

(72) Inventor: Michael Reynard, Santa Monica, CA (US)

( * ) Notice: Subject to any disclaimer, the term of this patent is extended or adjusted under 35 U.S.C. 154(b) by 0 days.

(21) Appl. No.: 19/203,945

(22) Filed: May 9, 2025

(51) Int. Cl.

| | |
|---|---|
| *A61B 5/1455* | (2006.01) |
| *A61B 3/00* | (2006.01) |
| *A61B 3/10* | (2006.01) |
| *A61B 5/00* | (2006.01) |

(Continued)

(52) U.S. Cl.
CPC .......... *A61B 5/1455* (2013.01); *A61B 3/0008* (2013.01); *A61B 3/10* (2013.01); *A61B 5/7267* (2013.01); *G01J 3/44* (2013.01); *G16H 50/20* (2018.01)

(58) Field of Classification Search
CPC ....... A61B 3/0008; A61B 3/10; A61B 5/1455; A61B 5/7267; G01J 3/44
See application file for complete search history.

(56) References Cited

U.S. PATENT DOCUMENTS

| | | | |
|---|---|---|---|
| 6,721,583 B1 * | 4/2004 | Durkin ............... | A61B 5/14532 600/476 |
| 7,508,524 B2 | 3/2009 | Mahadevan-Janse et al. | |
| 8,896,682 B2 | 11/2014 | Bressler et al. | |

(Continued)

FOREIGN PATENT DOCUMENTS

| | | |
|---|---|---|
| EP | 1383417 B3 | 12/2009 |
| EP | 2770326 A1 | 8/2014 |
| EP | 4057215 A1 | 9/2022 |

OTHER PUBLICATIONS

Woong Moon, S., Kim, W., Choi, S. and Shin, J.-H. (2016), Label-free optical detection of age-related and diabetic oxidative damage in human aqueous humors. Microsc. Res. Tech., 79: 1050-1055. https://doi.org/10.1002/jemt.22743 (Year: 2016).*

(Continued)

*Primary Examiner* — Charles A Marmor, II
*Assistant Examiner* — Andrew E Hoffpauir
(74) *Attorney, Agent, or Firm* — Richard A. Baker, Jr.

(57) ABSTRACT

A non-invasive diagnostic system is disclosed that integrates Raman spectroscopy with Artificial Intelligence (AI) to detect, classify, and quantify biomarkers and pharmacologic agents in the aqueous humor of the anterior chamber of the eye. The system includes a handheld or slit lamp-mounted Raman probe, a spectral acquisition and preprocessing pipeline, and an AI analysis engine trained to recognize disease-associated molecular signatures. The platform supports real-time diagnosis of glaucoma, uveitis, and other anterior segment conditions, enabling early detection, risk stratification, and longitudinal monitoring. The AI component is capable of incorporating newly discovered biomarkers and contextual factors such as medication use, diurnal variation, and anatomical sampling location. Diagnostic outputs are presented with confidence scores and may include disease classification, biomarker trends, or pharmacologic exposure levels. Built-in safety protocols ensure ANSI Z136.1-compliant laser use, while explainable AI tools and federated learning enhance transparency and clinical adaptability.

26 Claims, 8 Drawing Sheets

(51) Int. Cl.
*G01J 3/44*         (2006.01)
*G16H 50/20*      (2018.01)

(56)         References Cited

U.S. PATENT DOCUMENTS

| | | | |
|---|---|---|---|
| 10,993,840 | B2 | 5/2021 | Berlin |
| 12,201,425 | B1* | 1/2025 | Deligianni ........... A61B 5/4803 |
| 2004/0019283 | A1* | 1/2004 | Lambert ............ A61B 5/14532 |
| | | | 600/476 |
| 2006/0074282 | A1* | 4/2006 | Ward .................. A61B 5/1455 |
| | | | 600/476 |
| 2006/0166268 | A1* | 7/2006 | Grus .................... G01N 33/564 |
| | | | 435/7.1 |
| 2010/0003707 | A1 | 1/2010 | Ghaffariyah |
| 2010/0105098 | A1 | 4/2010 | Frederiske et al. |
| 2012/0188538 | A1* | 7/2012 | Patil ....................... G01N 21/65 |
| | | | 356/479 |
| 2014/0160434 | A1* | 6/2014 | Brown, Jr. ........... A61B 5/6821 |
| | | | 600/483 |
| 2016/0000378 | A1* | 1/2016 | Hall ........................ G06F 17/18 |
| | | | 702/19 |
| 2016/0331230 | A1* | 11/2016 | Liu ....................... A61B 5/0075 |
| 2017/0020460 | A1 | 1/2017 | LeBlond et al. |
| 2017/0049327 | A1 | 2/2017 | Alfano et al. |
| 2017/0202462 | A1 | 7/2017 | Motz et al. |
| 2017/0300654 | A1* | 10/2017 | Stein ........................ H04L 69/40 |
| 2020/0082282 | A1* | 3/2020 | Simpson ................ G06N 3/045 |
| 2021/0348234 | A1 | 11/2021 | Mootha et al. |
| 2022/0373466 | A1* | 11/2022 | Smith ..................... A61B 3/102 |
| 2023/0228744 | A1 | 7/2023 | Brady et al. |
| 2023/0240538 | A1 | 8/2023 | Yadav et al. |
| 2024/0027417 | A1* | 1/2024 | Vasefi .................... G01N 21/55 |
| 2024/0159588 | A1* | 5/2024 | Vakhshoori ........... G01J 3/0275 |
| 2024/0191238 | A1 | 6/2024 | Wyass-Corey et al. |
| 2024/0225451 | A1* | 7/2024 | Dunham .................. A61B 1/01 |
| 2024/0350257 | A1* | 10/2024 | Ma ......................... G02F 1/0121 |
| 2024/0371184 | A1* | 11/2024 | Comiter .............. G06N 3/0475 |
| 2024/0371496 | A1* | 11/2024 | Wang ...................... G16H 20/70 |
| 2025/0305962 | A1* | 10/2025 | Smith ...................... A61B 3/10 |

OTHER PUBLICATIONS

Selvaraju et al., "Grad-CAM: Visual Explanations from Deep Networks via Gradient-Based Localization," 2017 IEEE International Conference on Computer Vision (ICCV), Venice, Italy, 2017, pp. 618-626, doi: 10.1109/ICCV.2017.74 (Year: 2017).*

Kumamoto et al., Slit-scanning Raman microscopy: Instrumentation and applications for molecular imaging of cell and tissue. J. Appl. Phys. Nov. 7, 2022; 132 (17): 171101. https://doi.org/10.1063/5.0102079 (Year: 2022).*

Li et al., Harnessing the power of Raman spectroscopic imaging for ophthalmology. Front Chem. May 12, 2023;11:1211121. doi: 10.3389/fchem.2023.1211121. PMID: 37252371; PMCID: PMC10213270. (Year: 2023).*

Stiebing et al., Nonresonant Raman spectroscopy of isolated human retina samples complying with laser safety regulations for in vivo measurements. Neurophotonics. Oct. 2019;6(4):041106. doi: 10.1117/1.NPh.6.4.041106. Epub Sep. 3, 2019. PMID: 31482104; PMCID: PMC6718815. (Year: 2019).*

Imoro, I., 2020, Non-invasive Raman spectroscopy of Albumin in the aqueous humor of the anterior chamber of the eye [Master's thesis], University of South-Eastern Norway Faculty of Health and Social Sciences, https://openarchive.usn.no/usn-xmlui/handle/11250/2671845?show=full. (Year: 2020).*

Zhang et al., (2020). Dark-field illumination in conjunction with confocal Raman spectroscopy for real-time noninvasive aqueous humor investigation. Optical Engineering, 59(9), Article 092002. https://doi.org/10.1117/1.OE.59.9.092002 (Year: 2020).*

Han et al., Denoising and Baseline Correction Methods for Raman Spectroscopy Based on Convolutional Autoencoder: A Unified Solution. Sensors (Basel). May 16, 2024;24(10):3161. doi: 10.3390/s24103161. PMID: 38794016; PMCID: PMC11125329. (Year: 2024).*

Lambert et al., Glucose determination in human aqueous humor with Raman spectroscopy. J Biomed Opt. May-Jun. 2005;10(3):031110. doi: 10.1117/1.1914843. PMID: 16229635. (Year: 2005).*

Xiang et al., Region-resolved multi-omics of the mouse eye, Cell Reports, vol. 42, Issue 2, 2023, 112121, ISSN 2211-1247, https://doi.org/10.1016/j.celrep.2023.112121. (Year: 2023).*

Imoro. 2020. "Non-Invasive Raman Spectroscopy of Albumin in the Aqueous Humor of the Anterior Chamber of the Eye: An Initial in Vitro Validation of a Novel Slit Lamp Mounted Setup for Raman Spectroscopy of Proteins in the Aqueous Humor of the Living Eye Using a Customized Eye Model." USN Open Archive. (Year: 2020).*

Guo et al., Applications of Raman Spectroscopy in Ocular Biofluid Detection, Frontiers in Chemistry 12 (2296-2646), 2024, https://doi.org/10.3389/fchem.2024.1407754. (Year: 2024).*

Begoli, E., Bhattacharya, T., & Kusnezov, D. (2019). The need for uncertainty quantification in machine-assisted medical decision making. Nature Machine Intelligence, 1(1), 20-23.

Chen, Y., Li, S., Wang, W., et al. (2022). Aqueous Humor Biomarkers in Glaucoma Detection and Monitoring. Frontiers in Medicine, 9, 857919. https://doi.org/10.3389/fmed.2022.857919.

Chilamkurthy, S., Ghosh, R., Tanamala, S., Biviji, M., Campeau, N.G., Venugopal, V.K., Mahajan, V., Rao, P., & Warier, P. (2018). Deep learning algorithms for detection of critical findings in head CT scans: a retrospective study. The Lancet, 392(10162), 2388-2396.

Fernández-Vega Cueto A, Álvarez L, Garcia M, Álvarez-Barrios A, Artime E, Fernández-Vega Cueto L, Coca-Prados M, González-Iglesias H. Candidate Glaucoma Biomarkers: From Proteins to Metabolites, and the Pitfalls to Clinical Applications. Biology (Basel). Aug. 10, 2021;10(8):763. doi: 10.3390/biology10080763. PMID: 34439995; PMCID: PMC8389649.

Fiedorowicz E, Cieślińska A, Kuklo P, Grzybowski A. Protein Biomarkers in Glaucoma: A Review. J Clin Med. Nov. 18, 2021;10(22):5388. doi: 10.3390/jcm10225388. PMID: 34830671; PMCID: PMC8624910.

Kendall, A., & Gal, Y. (2017). What uncertainties do we need in Bayesian deep learning for computer vision? In Advances in Neural Information Processing Systems (pp. 5574-5584).

Lo Faro, V., Tenori, L., Tsagkaraki, M., et al. (2021). Biomarkers in Glaucoma: A Review on Proteomic and Metabolomic Studies of the Aqueous Humor. International Journal of Molecular Sciences, 22(12), 6488. https://doi.org/10.3390/ijms22126488.

Nucci, C., Di Pierro, D., Varesi, C., et al. (2013). Increased Malondialdehyde Concentration and Reduced Total Antioxidant Capacity in Aqueous Humor and Blood Samples from Patients with Glaucoma. Molecular Vision, 19, 1841-1846.

O'Hagan, A. (1999). Bayesian neural networks with confidence estimations applied to data mining. Computational Statistics & Data Analysis, 30(1), 99-122. ScienceDirect.

Pietrowska, K., Dmuchowska, D. A., Krasnicki, P., et al. (2021). Protein Biomarkers in Glaucoma: A Review. Journal of Clinical Medicine, 10(22), 5388. https://doi.org/10.3390/jcm10225388.

Reinehr, S., Mueller-Buehl, A. M., Tsai, T., Joachim, S. C. (2021). Specific Biomarkers in the Aqueous Humour of Glaucoma Patients. Klinische Monatsblätter für Augenheilkunde, 238(12), 1276-1283. https://doi.org/10.1055/a-1690-7468.

Sanjoy K. Bhattacharya; Richard K. Lee; Franz H. Grus; the Seventh ARVO/Pfizer Ophthalmics Research Institute Conference Working Group, Research Opportunities, Jan. 2013, Molecular Biomarkers in Glaucoma, Investigative Ophthalmology & Visual Science Jan. 2013, vol. 54, 121-131. doi:https://doi.org/10.1167/iovs.12-11067.

Stamer, W. D., & Overby, D. R. (2024). The Biology of Schlemm's Canal. In Reference Module in Neuroscience and Biobehavioral Psychology. Elsevier. https://doi.org/10.1016/B978-0-443-13820-1.00104-3.

Tsai, Y-C., Lee, H-P., Tsung, T-H., Chen, Y-H., Le, D-W., Unveiling Novel Structural Biomarkers for the Diagnosis of Glaucoma. Biomedicines. 2024:12,1211-1222. https://doi.org/10.3390/biomedicines12061211.

(56) References Cited

OTHER PUBLICATIONS

Von Thun Und Hohenstein-Blaul, N., Kunst, S., Pfeiffer, N. et al. Biomarkers for glaucoma: from the lab to the clinic. Eye 31, 225-231 (2017). https://doi.org/10.1038/eye.2016.300.

Wei, Q., Zhou, L., Sun, J., Wu, G., Gong, S., Gao, Z., Wu, J., Wang, Y., Xiao, Y., & Li, Y. (2025). Rapid Detection of Drugs in Blood Using "Molecular Hook" Surface-Enhanced Raman Spectroscopy and Artificial Intelligence Technology for Clinical Applications. Biosensors and Bioelectronics, 267, 116855. https://doi.org/10.1016/j.bios.2024.116855.

Workman Jr, J. (2025). Machine Learning-Enhanced SERS Technology Advances Cancer Detection. Spectroscopy Online. Available at: https://www.spectroscopyonline.com/view/machine-learning-enhanced-sers-technology-advances-cancer-detection (accessed Feb. 5, 2025).

Youngblood, H., Hauser, M. A., Liu, Y. (2019). Update on the Genetics of Primary Open-Angle Glaucoma. Experimental Eye Research, 188, 107795. https://doi.org/10.1016/j.exer.2019.107795.

Youssef Abdalla, Laura E. McCoubrey, Fabiana Ferraro, Lisa Maria Sonnleitner, Yannick Guinet, Florence Siepmann, Alain Hédoux, Juergen Siepmann, Abdul W. Basit, Mine Orlu, David Shorthouse, Machine learning of Raman spectra predicts drug release from polysaccharide coatings for targeted colonic delivery, Journal of Controlled Release, vol. 374, 2024, pp. 103-111, ISSN 0168-3659, https://doi.org/10.1016/j.jconrel.2024.08.010.

Pelletier CC, Lambert JL, Borchert M. Determination of Glucose in Human Aqueous Humor Using Raman Spectroscopy and Designed-Solution Calibration. Applied Spectroscopy. 2005;59(8):1024-1031. doi:10.1366/0003702054615133.

Theoharia I. Sideroudi, Nikolaos M. Pharmakakis, George N. Papatheodorou, George A. Voyiatzis. Non-invasive detection of antibiotics and physiological substances in the aqueous humor by Raman spectroscopy. Lasers in Surgery and Medicine. 38, 7: 695-703. https://doi.org/10.1002/lsm.20360.

Amin, Mohamed, et al. Detection and identification of drug traces in latent fingermarks using Raman spectroscopy. Nature Scientific Reports. (2022) 12:3136. https://doi.org/10.1038/s41598-022-07168-6.

Jaworska, Aleksandra, et al. Potential of Surface Enhanced Raman Spectroscopy(SERS) in Therapeutic Drug Monitoring (TDM). ACritical Review. Biosensors (Basel). Sep. 19, 2016;6(3):47. https://doi.org/10.3390/bios6030047.

Pandey, Rishikesh, et al. Noninvasive Monitoring of Blood Glucose with Raman Spectroscopy. Acc. Chem. Res. 2017, 50, 2, 264-272. https://doi.org/10.1021/acs.accounts.6b00472.

Shao J, Lin M, Li Y, Li X, Liu J, Liang J, et al. (2012) In Vivo Blood Glucose Quantification Using RamanSpectroscopy. PLoS One 7(10): e48127. https://doi.org/10.1371/journal.pone.0048127.

Pors, Anders, et al. Calibration and performance of a Raman-based device for non-invasive glucose monitoring in type 2 diabetes. Nature Scientific Reports. (2025) 15:10226. https://doi.org/10.1038/s41598-025-95334-x.

Wang, YIngbin, et al. Rapid detection of drug abuse via tear analysis using surface enhanced Raman spectroscopy and machine learning. Nature Scientific Reports. (2025) 15:1108. https://doi.org/10.1038/s41598-025-85451-y.

Acikoz, Gunes. Illicit Drug Analysis in Blood Samples withMultivariate Analysis Using Surface-EnhancedRaman Spectroscopy. Spectroscopy Supplements. Raman Technology for Today's Spectroscopists. vol. 38, Issue S6. pp. 20-27. https://doi.org/10.56530/spectroscopy.er607615.

Goodacre, Roy. Developing SERS Methods for Drug Detection. SpectroscopyOnline. https://www.spectroscopyonline.com/view/developing-sers-methods-drug-detection.

Sun, Xiangcheng. Glucose detection through surface-enhanced Ramanspectroscopy: A review. Anal Chim Acta. May 8, 2022:1206:339226. doi: 10.1016/j.aca.2021.339226.

Sikkel, Markus, et al. High speed sCMOS-based oblique plane microscopy applied to the study ofcalcium dynamics in cardiac myocytes. Journal of Biophotonics / vol. 9, Issue 3 / p. 311-323. https://doi.org/10.1002/jbio.201500193.

Huang, Xueqin, et al. Real-time SERS monitoring anticancer drug release along with SERS/MR imaging for pHsensitive chemo-phototherapy. Acta Pharmaceutica Sinica B 2023;13(3):1303e1317. https://doi.org/10.1016/j.apsb.2022.08.024.

Parachalil, Drishya, et al. Raman spectroscopy as a potential tool for label free therapeutic drug monitoring in humanserum: the case of busulfan and methotrexate. Analyst. Issue 17, 2019.

Ochiai, Yuko, and Haruyuki Ochiai. "Higher Concentration of Transforming Growth Factor-Beta in Aqueous Humor ofGlaucomatous Eyes and Diabetic Eyes." Japanese Journal of Ophthalmology 46, No. 3 (2002): 249-253. https://doi.org/10.1016/S0021-5155(01)00523-8.

Tripathi RC, Li J, Chan WF, Tripathi BJ. "Aqueous humor in glaucomatous eyes contains an increased level of TGF beta 2." Experimental Eye Research. Dec. 1994;59(6):723 727. doi:10.1006/exer.1994.1158.

Picht G, Welge Lüssen U, Grehn F, Lütjen Drecoll E. "Transforming growth factor beta 2 levels in the aqueous humor in different types of glaucoma and the relation to filtering bleb development." Graefe's Archive for Clinical and Experimental Ophthalmology. 2001;239:199 207. Nature.

* cited by examiner

AI-ASSISTED RAMAN SPECTROSCOPY SYSTEM FOR BIOMARKER ANALYSIS OF AQUEOUS HUMOR

CROSS-REFERENCE TO RELATED APPLICATIONS

This is a priority patent application. This US Patent Application is simultaneously filed with a US Patent Application titled "AI-Assisted Raman Spectroscopy for Diagnosis and Analysis of Intraocular Tumors" by inventor Michael Reynard, said application incorporated herein by reference in its entirety.

BACKGROUND

Field of the Inventions

The disclosed AI-assisted Raman diagnostic system relates to non-invasive ophthalmic diagnostics, particularly to systems and methods that utilize Raman spectroscopy enhanced by artificial intelligence to analyze biomarkers in aqueous humor. The inventions are especially applicable to the detection and monitoring of glaucoma, uveitis, and other anterior segment ocular diseases.

Background of the Inventions

Glaucoma is a leading cause of irreversible blindness, characterized by progressive optic nerve damage often associated with elevated intraocular pressure (IOP). Traditional diagnostics rely on structural imaging and pressure measurements, which may not reflect early biochemical changes. Raman spectroscopy offers a non-destructive method to detect molecular signals in biological fluids, including aqueous humor. Measurable molecular signals indicative of a physiological condition or disease are collectively referred to as biomarkers. Detection refers to identifying those specific signals in the data. However, interpreting complex spectral data may require advanced computational methods. Applying AI flags specific spectral features that match known or learned biomarkers of glaucoma, like elevated matrix metalloproteinases, oxidative stress markers, or altered extracellular matrix proteins. These biomarkers provide a molecular-level understanding of the disease process.

BRIEF SUMMARY

In one aspect, a system for non-invasive glaucoma detection includes: a Raman spectroscopy probe adapted for anterior chamber analysis, a spectral data acquisition module that reads light output from the Raman spectroscopy probe and produces a Raman spectra, and an artificial intelligence engine trained to identify the Raman spectra and quantify known and previously undiscovered biomarkers, the artificial intelligence engine including at least one artificial intelligence model.

The artificial intelligence engine includes convolutional neural networks (CNNs) for pattern recognition in Raman spectra. The Raman spectroscopy probe may be configured to be mounted on a slit lamp. The system may also include a graphical user interface for visualizing diagnostic results, biomarker trends, and disease risk scores. The artificial intelligence engine may include autoencoders for baseline correction and noise filtering. The artificial intelligence engine may integrate Raman data with optical coherence tomography (OCT) or intraocular pressure (IOP) data. The system may also include where the known and previously undiscovered biomarkers include but are not limited to TGF-$\beta$2, MMPs, TIMPs, fibronectin, oxidative stress markers, or miRNAs. The system may also be configured for longitudinal monitoring of disease progression. The Raman spectroscopy probe includes a laser excitation source. The artificial intelligence engine is configured to incorporate newly identified spectral biomarkers based on training from updated clinical datasets or user-validated input. The Raman spectroscopy probe includes optical safety sensors and alignment tracking to ensure safe operation during anterior chamber measurement. The system for non-invasive glaucoma detection detects signal loss or misalignment and halts laser activation in response to potential safety risks. The artificial intelligence engine includes an explainability module configured to highlight spectral features contributing to classification decisions. At least one Artificial Intelligence model is trained using federated learning across distributed clinical sites and is adaptable to include newly discovered biomarkers. The Raman spectroscopy probe comprises surface-enhanced Raman spectroscopy (SERS) capability and is operable with or without confocal optical elements. The system is configured to capture spectral data in a range of 400 to 1800 cm$^{-1}$. The system may also include where Raman signal acquisition includes temporal averaging of multiple spectra to increase signal-to-noise ratio under clinical lighting conditions. At least one artificial intelligence model is trained to identify spectral biomarkers specific to glaucomatous changes in the trabecular meshwork, including known and previously undiscovered biomarkers. The Artificial Intelligence engine is configured to incorporate newly identified spectral biomarkers based on training from updated clinical databases or user-validated input. The Raman spectroscopy probe emits laser radiation at a power and wavelength within ocular safe exposure limits as defined by ANSI Z136.1 or ISO 15004. The Raman spectroscopy probe emits laser energy at a power and divergence classified as Class 1M or Class 3R under ANSI Z136.1, ensuring maximum permissible exposure is not exceeded during use on a human eye.

In one aspect, a method of detecting ocular biomarkers using Raman spectroscopy, includes: projecting a Raman excitation beam into an anterior chamber of an eye, acquiring spectral data from aqueous humor in the anterior chamber from the Raman excitation beam at a recorded time of day, analyzing the spectral data using an artificial intelligence model that compensates for time-of-day-dependent biomarker fluctuations, where the artificial intelligence model adjusts diagnostic interpretation based on known diurnal variation in molecular biomarker expression, and outputting the diagnostic interpretation.

In one aspect, a method of estimating intraocular pressure-related molecular stress in an eye, includes: acquiring Raman spectral data from aqueous humor in the eye, identifying spectral features corresponding to biomarkers modulated by elevated intraocular pressure, and analyzing said spectral features using an artificial intelligence model trained to correlate Raman peak variations with intraocular pressure-associated biochemical profiles to determine an estimated intraocular pressure, and outputting the estimated intraocular pressure.

In one aspect, a method of analyzing Raman spectral data from aqueous humor of an eye, includes receiving Raman spectral input from a sample of the aqueous humor obtained from an anterior chamber of the eye of a subject, receiving user-provided or system-imported data indicating current topical or systemic medications, dosage, and regimen taken by the subject, adjusting a diagnostic interpretation of spectral features using an artificial intelligence model trained to account for pharmacologic influences on biomarker expression, where the artificial intelligence model modifies classification thresholds or interpretive weights based on known or inferred effects of said medications on target biomarker concentrations, and outputting the diagnostic interpretation.

In one aspect, a method of interpreting Raman spectral data from aqueous humor using an artificial intelligence system, includes: receiving input spectral data from a Raman spectroscopy device examining an eye of a subject, receiving associated contextual metadata including one or more of an age, sex, medication use, systemic conditions, ocular history, and environmental factors of the subject, and adjusting a diagnostic analysis of said spectral data based on known or learned influences of a contextual metadata on biomarker expression, where the artificial intelligence system outputs a diagnosis and a reliability score that reflects contextual conditions of the eye.

In one aspect, a method for evaluating a diagnostic reliability of Raman spectroscopy in ocular biomarker detection, includes: acquiring Raman spectral data from an anterior chamber of an eye using a handheld or slit lamp-mounted Raman probe; preprocessing the Raman spectral data to remove noise, correct baselines, and normalize intensities; analyzing the Raman spectral data using an artificial intelligence model configured to: (a) evaluate signal quality metrics including signal-to-noise ratio, baseline flatness, peak clarity, and spectral completeness; (b) generate a signal-based confidence score representing a likelihood that the Raman spectral data meets diagnostic quality thresholds; determining a sampling location modifier based on (a) probe metadata indicating anatomical sampling position, or (b) spectral features indicative of central or peripheral chamber origin, computing a reliability adjustment factor based on historical biomarker fidelity by location and known diffusion characteristics, outputting a diagnostic interpretation accompanied by: (a) a confidence value indicating spectral integrity, and (b) a location-based reliability annotation reflecting anatomical context.

In one aspect, a non-invasive diagnostic system for analyzing biomarkers in aqueous humor of an anterior chamber of an eye, includes: a Raman spectroscopy probe configured to direct excitation light through a cornea and receive Raman-scattered light from biomolecules in the aqueous humor, a mounting adapter configured to attach the Raman spectroscopy probe to a slit lamp, a spectrometer operatively coupled to the Raman spectroscopy probe and configured to acquire Raman spectra from the aqueous humor, a computing system includes a processor and a memory storing machine-readable instructions which, when executed, cause the non-invasive diagnostic system to: (a) denoise and normalize the Raman spectra using an artificial intelligence model, (b) identify spectral features corresponding to known and candidate biomarkers of ocular disease, (c) quantify concentrations of identified biomarkers, and (d) classify the Raman spectra into a diagnostic category including but not limited to glaucoma, uveitis, or normal, where the computing system generates a diagnostic output based on a classification and displays said diagnostic output to a user.

The Raman spectroscopy probe is a handheld device that is removably mounted to a slit lamp adapter. The artificial intelligence model includes a convolutional neural network trained to classify spectral features associated with oxidative stress, extracellular matrix remodeling, inflammatory cytokines, or neurodegenerative markers. The diagnostic output includes but is not limited to a quantified concentration of at least one of: TGF-β2, fibronectin, 8-hydroxy-2'-deoxyguanosine (8-OHdG), matrix metalloproteinase-9 (MMP-9), or interleukin-6. The artificial intelligence model may include a regression layer trained to estimate biomarker concentration based on peak intensity and location within the Raman spectra. The computing system is further configured to integrate the diagnostic output with structural imaging data or intraocular pressure measurements for multimodal disease profiling. The computing system further stores a database of normative Raman spectra and uses the database to compute deviation scores for each patient. The diagnostic output includes a disease risk score generated using a supervised machine learning model trained on labeled spectral data. The spectrometer is configured to detect Raman shifts in a range of 400 cm−1 to 1800 cm−1. The non-invasive diagnostic system is configured to transmit spectral data to a cloud-based AI platform for remote processing and receive diagnostic results. The Raman spectroscopy probe includes an excitation laser operating at a wavelength between 785 nm and 850 nm. The computing system is configured to monitor changes in biomarker concentrations over time and display trend graphs. The computing system is configured to recommend clinical actions based on the diagnostic category, such as referral, additional testing, or treatment escalation.

In one aspect, a method for non-invasively detecting disease-related novel or emerging biomarkers in aqueous humor using AI-assisted Raman spectroscopy, includes steps of: (a) acquiring Raman spectra from an anterior chamber via a handheld or mounted Raman probe, (b) denoising and preprocessing the Raman spectra using AI algorithms, (c) identifying and quantifying disease-related biomarkers in the Raman spectra into a spectral profile, (d) classifying the spectral profile into a diagnostic category, and (e) displaying a diagnostic output including disease status and biomarker levels. A computer-readable medium includes machine-readable instructions that, when executed by a processor, perform the steps may also include.

In one aspect, a system for non-invasive biomarker detection in an anterior chamber of an eye using Raman spectroscopy, includes: a Raman spectroscopy probe configured to project an excitation beam along a central optical axis and acquire Raman spectra from a central region of the anterior chamber, a computing system operatively coupled to the Raman spectroscopy probe and includes a processor and a memory storing machine-readable instructions which, when executed, cause the system to: (a) perform spectral acquisition and preprocessing including normalization and denoising on the Raman spectra to create spectral data, (b) analyze the spectral data using an artificial intelligence model trained to classify existing and newly discovered disease-relevant biomarkers dispersed within the anterior chamber, (c) estimate a confidence score for each scan, based on one or more of: (i) intrinsic spectral signal quality, (ii) anatomical sampling location, (iii) model prediction variance, (iv) inter-model agreement, (d) output a diagnostic classification with an associated confidence value or category, where the system is further configured to generate a user-facing notification when confidence scores fall below a predefined threshold, indicating a potential need for resampling or additional testing. The system may also include where the artificial intelligence model is further configured to: perform temporal averaging of multiple sequential spectra acquired during a single scan session to increase signal-to-noise ratio, apply time-based normalization protocols to account for diurnal biomarker variation, infer anatomical sampling location from spectral signal features when metadata on probe position is unavailable, and adjust the confidence score dynamically based on these inferred or computed parameters. The system may also include where the artificial intelligence model is further configured to perform temporal averaging of multiple sequential spectra acquired during a single scan session to increase signal-to-noise ratio, apply time-based normalization protocols to account for diurnal biomarker variation, infer anatomical sampling location from spectral signal features when metadata on probe position is unavailable, and adjust the confidence score dynamically based on these inferred or computed parameters.

In one aspect, a system for non-invasive biomarker detection in an anterior chamber of an eye using Raman spectroscopy, includes: a Raman spectroscopy probe configured to project an excitation beam along a central optical axis and acquire Raman spectra from a central region of the anterior chamber, a computing system operatively coupled to the Raman spectroscopy probe and includes a processor and a memory storing machine-readable instructions which, when executed, cause the system to: (a) perform spectral acquisition and preprocessing including normalization and denoising on the Raman spectra creating spectral data, (b) analyze the spectral data using an artificial intelligence model trained to classify disease-relevant biomarkers dispersed within the anterior chamber, (c) estimate a confidence score for each scan based on one or more of: (i) intrinsic spectral signal quality, (ii) anatomical sampling location, (iii) model prediction variance, (iv) inter-model agreement, (d) output a diagnostic classification with an associated confidence value or category, where the system is further configured to generate a user-facing notification when confidence scores fall below a predefined threshold, indicating a potential need for resampling or additional testing.

In one aspect, a system for detecting and quantifying pharmacologic agents in an anterior chamber of an eye using Raman spectroscopy, includes: a Raman probe configured to acquire spectral data from aqueous humor in the anterior chamber, a spectrometer configured to detect Raman-shifted light in a range of 400 to 1800 cm 1, a computing system includes an artificial intelligence model trained to identify Raman spectral features corresponding to one or more ophthalmic drugs, a concentration estimation module configured to quantify said compounds based on learned regression models, where the system outputs an identity of the one or more ophthalmic drugs and a concentration of the one or more ophthalmic drugs with respect to therapeutic reference ranges.

In one aspect, a system for non-invasive ocular diagnosis using Raman spectroscopy, includes: a Raman probe configured to acquire spectral data from aqueous humor of an anterior chamber of an eye, an artificial intelligence model trained to detect Raman spectral features in the spectral data corresponding to pharmaceutical agents, where the pharmaceutical agents serve as surrogate biomarkers that inform disease state, therapeutic engagement, or patient adherence.

The system may also include where the pharmaceutical agents comprise one or more of: prostaglandin analogs, beta-blockers, alpha-2 adrenergic agonists, carbonic anhydrase inhibitors, corticosteroids, or immunomodulatory drugs. The system may also include where a presence or absence of the pharmaceutical agents modifies a diagnostic interpretation of concurrent biomarker profiles. The system may also include where the artificial intelligence model is configured to estimate a concentration of the pharmaceutical agents and compare the concentration to therapeutic reference ranges to assess treatment adherence or dosing efficacy.

Other technical features may be readily apparent to one skilled in the art from the following figures, descriptions, and claims.

In one aspect, a method for using pharmaceutical agents as surrogate biomarkers in AI-assisted Raman spectral analysis of aqueous humor, includes: (a) acquiring Raman spectra from an anterior chamber of an eye, (b) identifying spectral features corresponding to one or more pharmaceutical agents, (c) interpreting the one or more pharmaceutical agents as surrogate indicators of disease treatment, therapeutic response, or patient compliance, (d) modifying a diagnostic interpretation of endogenous biomarkers based on a presence or absence of said pharmaceutical agents, and (e) outputting the diagnostic interpretation.

The method may also include comparing an estimated concentration of the pharmaceutical agents to known therapeutic ranges to determine whether the disease treatment is subtherapeutic, therapeutic, or supratherapeutic.

In one aspect, a method for detecting ophthalmic medications in an eye using Raman spectroscopy, includes: acquiring Raman spectra from an anterior chamber of the eye, denoising and preprocessing the Raman spectra into spectral features, analyzing spectral features using a pharmacologic AI model, estimating a concentration of detected medications, and displaying an output indicating an identity, concentration, and pharmacologic status of each medication.

In one aspect, a method of analyzing Raman spectral data from aqueous humor of an eye, includes: receiving Raman spectral input from a sample obtained from an anterior chamber of the eye of a subject, receiving user-provided or system-imported data indicating current topical or systemic medications taken by the subject, adjusting a diagnostic interpretation of spectral features using an artificial intelligence model trained to account for pharmacologic influences on biomarker expression, where the artificial intelligence model modifies classification thresholds or interpretive weights based on known or inferred effects of said medications on target biomarker concentrations.

In one aspect, an AI-assisted Raman diagnostic system for non-invasive analysis of biomarkers and pharmacologic agents in aqueous humor of an eye, the AI-assisted Raman diagnostic system includes: a Raman spectroscopy module configured to collect spectral data from the aqueous humor, an artificial intelligence engine configured to process the spectral data and output diagnostic interpretations, a modular software architecture includes one or more independently updateable components selected from: (i) neural network model weights, (ii) signal preprocessing algorithms, (iii) biomarker classification modules, (iv) pharmacologic detection modules, (v) clinical protocol templates, (vi) spectral normalization layers, and (vii) user interface modules, where the AI-assisted Raman diagnostic system is configured to receive, validate, and deploy modular updates without requiring retraining or reinstallation of the artificial intelligence engine.

The artificial intelligence engine is further configured to accommodate updates reflecting changes in Raman spectroscopy instrumentation, including changes to excitation wavelength, detector sensitivity, or optical resolution. The AI-assisted Raman diagnostic system may also include where modular updates are performed using version-controlled packages that can be deployed locally or via a secure network. The AI-assisted Raman diagnostic system may also include where the modular software architecture enables incorporation of newly discovered biomarkers by adding new spectral templates and corresponding AI classification logic without altering pre-existing biomarker interpretations. The AI-assisted Raman diagnostic system may also include where pharmacologic detection modules are updatable to reflect changes in therapeutic compounds, drug formulations, or Raman-active pharmaceutical agents introduced into clinical practice. The AI-assisted Raman diagnostic system may also include where clinical protocol modules are updatable to align with revised diagnostic criteria, treatment guidelines, or regulatory standards. The AI-assisted Raman diagnostic system may also include where updates to preprocessing algorithms include adjustments to baseline correction, spectral smoothing, and normalization in response to new Raman spectrometer configurations. The AI-assisted Raman diagnostic system may also include a federated learning framework configured to update AI model parameters based on distributed training across multiple clinical sites without centralizing patient data. The AI-assisted Raman diagnostic system may also include a user interface module, where updates to the user interface module include enhancements to explainability tools, display formatting, or workflow integration without modifying the AI-assisted Raman diagnostic system. The AI-assisted Raman diagnostic system may also include where a compliance module is configured to receive security and privacy updates to ensure adherence to applicable data protection regulations without disrupting system diagnostics.

The system may also include a safety subsystem that regulates an output of the laser excitation source to conform to ANSI Z136.1 ocular exposure limits. The system may also include where said safety subsystem includes a laser modulation circuit connected to the laser excitation source and timed pulse delivery mechanism. The system may also include where the laser excitation source operates at 785 nm±5 nm to optimize Raman signal quality and ocular safety. The system may also include where the laser excitation source operates in pulsed or time-gated mode to reduce cumulative energy exposure to ocular tissues. The system may also include where the safety subsystem monitors and limits a duration and intensity of exposure to the laser excitation source based on prognosis.

In one aspect, a method for detecting the presence of pharmaceutical or illicit drugs not primarily associated with ocular conditions in the aqueous humor using Raman spectroscopy, the method includes acquiring Raman spectral data from the anterior chamber of the eye, preprocessing the Raman spectral data to reduce fluorescence and noise, applying an artificial intelligence model trained to detect molecular vibrational signatures of drugs, and generating a diagnostic output indicating presence and estimated concentration of the drugs.

The method may also include where the identified drug or metabolite is used as a surrogate marker for systemic medical conditions, including diabetes, psychiatric disorders, epilepsy, or infectious disease. The method may also include wherein the drug is an illicit substance selected from the group consisting of cocaine, heroin, methamphetamine, fentanyl, $\Delta^9$-tetrahydrocannabinol (THC), and MDMA, and where detection is performed via a fixed-position, surface-enhanced Raman spectroscopy (SERS) probe configured to interface non-invasively with the anterior segment of the eye, without the introduction of free nanoparticles into the ocular environment. The method may further includes a regression model configured to estimate drug concentration and compare the estimated value to a therapeutic or toxic reference range.

In one aspect, a method for estimating glucose concentration in the aqueous humor using confocal Raman spectroscopy and artificial intelligence, the method includes: enhancing glucose-specific vibrational signals via a fixed, SERS-active substrate positioned at or near the corneal interface, applying an AI model trained on Raman-glucose calibration spectra from anterior chamber fluid samples, and interpreting the estimated glucose concentration as a correlational proxy for systemic glucose levels, without replacing systemic glucose monitoring unless validated through calibration.

In one aspect, a method for detecting pharmacologic adherence using Raman analysis of the aqueous humor, the method includes: identifying the presence or absence of known therapeutic agents in the aqueous humor using Raman spectroscopy, and inferring patient compliance or recent ingestion based on detection results. Other technical features may be readily apparent to one skilled in the art from the following figures, descriptions, and claims

BRIEF DESCRIPTION OF THE DRAWINGS

To easily identify the discussion of any particular element or act, the most significant digit or digits in a reference number refer to the figure number in which that element is first introduced.

DETAILED DESCRIPTION

Figure 1:
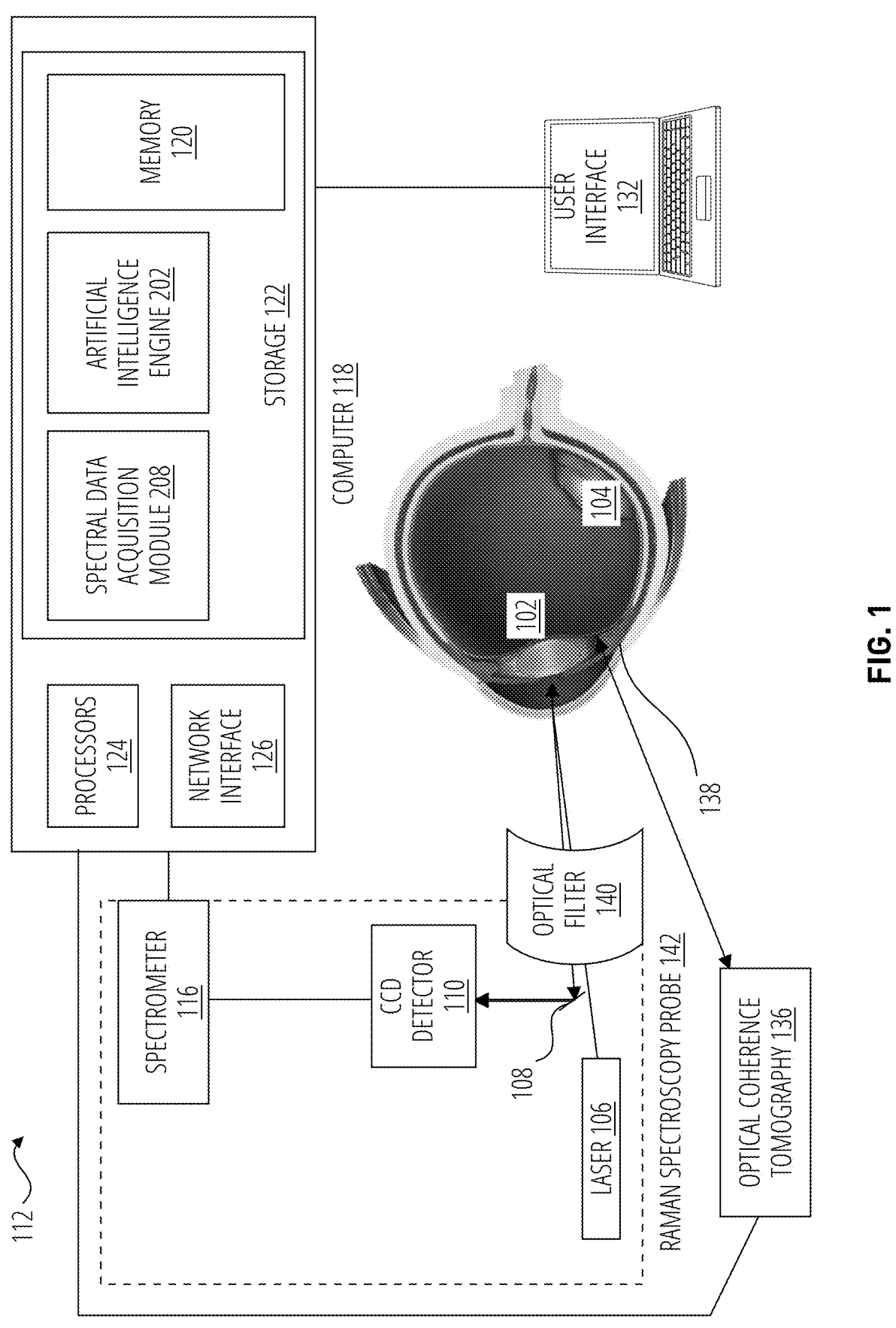
FIG. 1 depicts a representative system architecture of the AI-enhanced Raman spectroscopy diagnostic system.

These inventions provide a non-invasive diagnostic system that combines Raman spectroscopy and artificial intelligence to detect glaucoma-related biomarkers in the aqueous humor 138. See Table 1: Biomarkers Detectable via Raman Spectroscopy and their AI Interpretation. The system enables early diagnosis, disease staging, and longitudinal monitoring by capturing Raman spectra from the anterior chamber using a handheld or slit lamp-mounted Raman spectroscopy probe 142. The system's embedded AI analyzes spectral data in real time, classifies disease severity, and supports safe, repeatable clinical use via ANSI-compliant laser controls.

TABLE 1

| Biomarkers Detectable via Raman Spectroscopy and their AI Interpretation | | | |
| --- | --- | --- | --- |
| Biomarker | Raman Shift (cm$^{-1}$) | Clinical Relevance | AI Analysis Method |
| TGF-β2 | ~1005, ~1655 | Fibrosis in TM and SC | CNN-based classifier + regression analysis |

TABLE 1-continued

Biomarkers Detectable via Raman Spectroscopy and their AI
Interpretation

| Biomarker | Raman Shift $(cm^{-1})$ | Clinical Relevance | AI Analysis Method |
|---|---|---|---|
| 8-OHdG | ~734, ~1450 | Oxidative stress marker in glaucoma | Denoising autoencoder + logistic regression |
| Fibronectin | ~1335, ~1650 | ECM deposition, TM dysfunction | PCA + SVM classification |
| MMP-9 | ~1440, ~1585 | ECM remodeling, inflammation | XGBoost for biomarker level estimation |
| Myocilin | ~1250, ~1340 | Mutational aggregate in TM (juvenile POAG) | Neural network-based anomaly detection |
| Interleukin-6 | ~1000-~1500 (broad) | Inflammatory signaling | Temporal trend analysis + supervised ML |
| Ceramides/ Sphingolipids | ~1050, ~1300 | Apoptotic membrane markers | CNN-LSTM fusion model for time series |

The integration of artificial intelligence, particularly machine learning and deep learning models, offers a transformative opportunity to enhance Raman signal processing, biomarker identification, and clinical decision support in real-time. Such a system could allow for detection of disease states using molecular biomarkers, prior to visible clinical signs or structural damage.

These inventions address the longstanding need for a non-invasive, real-time, and AI-enhanced system for the detection and monitoring of anterior segment ocular diseases using Raman spectroscopy of aqueous humor 138

Overview of the Inventions

The disclosed AI-assisted Raman diagnostic system introduces a novel and integrated system for the non-invasive diagnosis and monitoring of anterior segment ocular diseases, primarily glaucoma, through the analysis of biomarkers in the aqueous humor 138 using Raman spectroscopy enhanced by artificial intelligence. This diagnostic system represents a shift from structural and pressure-based diagnostics to molecular profiling, enabling earlier and more personalized detection.

At its core, the system features a compact, precision-engineered Raman spectroscopy probe 142, designed for dual use: it may be operated as a handheld device or mounted onto a slit lamp using a dedicated adapter. This mounting capability addresses the inherent challenge of patient and operator stability, for instance, during spectral acquisition of delicate intraocular structures.

The Raman spectroscopy probe 142 directs a near-infrared laser beam through the cornea into the anterior chamber, where inelastic scattering of light—Raman scattering—interacts with biomolecules suspended in the aqueous humor 138. The backscattered signal, rich in molecular information, is collected through the same optical path and directed to a spectrometer for digitization.

Once acquired, the spectral data undergo real-time preprocessing facilitated by artificial intelligence. Advanced denoising algorithms, such as autoencoders and deep-learning-based baseline correction models, purify the signal by suppressing background fluorescence and stochastic noise while preserving relevant molecular signatures. This ensures that even weak Raman signals from low-concentration biomarkers remain interpretable.

Following preprocessing, the data passes through an intelligent feature extraction and classification engine. Here, convolutional neural networks or other machine learning frameworks analyze the spectral patterns to identify disease-specific biomarkers such as TGF-β2, fibronectin, MMPs, 8-OHdG, and neurodegenerative proteins. These markers, each associated with distinct Raman signatures, allow the system to recognize molecular changes correlated with the onset or progression of glaucoma and other anterior segment conditions such as uveitis.

The inventions may deploy a convolutional neural network (CNN) which scans the spectral data to detect important peaks and shapes—these might correspond to biochemical compounds like collagen, elastin, or glycosaminoglycans that change in glaucoma. These extracted features are compact, meaningful representations of the original data, reducing noise and focusing on the molecular "fingerprints" that matter.

The inventions may also include a quantification layer wherein AI regression models are used to estimate the concentration of identified biomarkers in real time. These values are not merely reported as raw data; rather, the system synthesizes them into an intelligible diagnostic output. This may include a disease probability score, a risk stratification model, or trend tracking over time, rendering the system ideal not only for diagnosis but for longitudinal disease monitoring. Risk stratification is a nuanced estimate based on molecular changes, possibly before clinical signs appear. This allows for early intervention or closer monitoring based on risk level.

The user interface provides intuitive visualizations of the molecular profile, spectral overlays for comparison, and diagnostic interpretations, which can be integrated into the patient's electronic health record. Furthermore, the system is built to be interoperable with additional data sources such as IOP measurements and OCT findings, enabling multimodal fusion and enhancing clinical decision support.

In doing so, the inventions bridge the gap between molecular ophthalmology and practical clinical tools, delivering a fully integrated platform capable of detecting early-stage pathology, guiding treatment decisions, and refining individualized care for patients with glaucoma and other ocular conditions.

The inventions provide a Raman spectroscopy system enhanced by AI to analyze aqueous humor biomarkers such as TGF-β2, MMPs, TIMPs, fibronectin, and oxidative stress markers. The system includes:

A Raman spectroscopy probe 142 (handheld or slit lamp-mounted)

Spectral acquisition hardware

Signal preprocessing modules (baseline correction, denoising)

AI analysis engine (CNNs, regression models, classification algorithms, explainable AI)

A user interface displaying diagnostic insights

Safety mechanisms to regulate laser exposure per ANSI Z136.1

The AI models classify glaucoma stage, quantify biomarkers, and generate a risk score. The system supports longitudinal monitoring, integrates with OCT and IOP data, and includes onboard diagnostics to ensure operational safety and clinical accuracy.

Selection of AI Architecture

The selection of an appropriate Artificial Intelligence (AI) architecture assists in the effectiveness, accuracy, and clinical reliability of an AI-enhanced Raman spectroscopy diagnostic system 112 for glaucoma. (See Table 1: AI Architecture Selection and Functional Attributes for Raman-Based Glaucoma Diagnosis). Unlike general-purpose machine learning models, the AI system in these inventions address the unique spectral complexity of biological tissues and fluids, the inter-patient variability in Raman signal profiles, and the subtle molecular differences between glaucomatous and non-glaucomatous eyes.

TABLE 1

AI Architecture Selection and Functional Attributes for
Raman-Based Glaucoma Diagnosis

| Category | Details |
|---|---|
| Model Architecture | Hybrid CNN + RNN (LSTM) |
| Purpose of CNN | Extract localized spectral features (e.g., peak detection, molecular vibration patterns) |
| Purpose of RNN (LSTM) | Analyze temporal or sequential data across multiple spectra from the same patient |
| Training Dataset | Raman spectra from glaucomatous and non-glaucomatous eyes, stratified by age, race, and disease stage |
| Data Augmentation | Spectral jittering, additive noise, baseline shifting, and synthetic spectra generation for class balancing |
| Generalization Strategy | Transfer learning + stratified cross-validation |
| Interpretability Module | Attention mechanisms and Grad-CAM for feature attribution |
| Personalization Mechanism | Longitudinal spectral learning + adaptive thresholding based on patient history |
| Risk Stratification Output | AI generates glaucoma risk levels: Low/Moderate/High with supporting biomarker signature map |
| Deployment Environment | Edge computing optimized (e.g., embedded GPU or on-slit lamp computing module) |
| Real-Time Capability | Yes-optimized for sub-second inference per spectrum |
| Update Mechanism | Continual learning module enabled for physician-supervised periodic updates |
| Fail-Safe Design | Fallback diagnostic pathways and clinician override capability |
| Integration Mode | Compatible with handheld and slit lamp-mounted Raman probe configurations |

To meet these demands, a hybrid AI approach was chosen, integrating convolutional neural networks (CNNs) for spectral feature extraction with recurrent neural networks (RNNs), such as long short-term memory (LSTM) units, for contextual sequence learning. This hybrid model enables the AI-enhanced Raman spectroscopy diagnostic system 112 to capture both local signal anomalies and broader patterns across the Raman spectral domain. The CNN component is particularly effective in detecting sharp spectral peaks associated with specific molecular vibrations, while the RNN component supports temporal learning across spectra collected over time from the same patient. Model selection also took into account the necessity of generalizability.

AI Framing and Training Protocol

Training was conducted on large, diverse datasets incorporating spectral data from patients across age groups, ethnicities, disease severities, and ocular comorbidities. Techniques such as stratified cross-validation and transfer learning were employed to reduce overfitting and to allow the artificial intelligence engine 202 to adapt to unseen data distributions, useful in a heterogeneous condition like glaucoma.

Another core requirement was interpretability. Clinicians must trust AI-generated diagnostic decisions, particularly when outcomes may influence the initiation of treatment or surgical intervention. To this end, the AI-enhanced Raman spectroscopy diagnostic system 112 may include attention mechanisms and gradient-based class activation mapping (Grad-CAM), allowing the AI to highlight specific spectral features that contributed to its decision. This fosters a collaborative diagnostic environment where physicians can interrogate and validate the AI's findings.

Finally, deployment considerations may shape the AI architecture. The AI-enhanced Raman spectroscopy diagnostic system 112 may be designed for real-time inference on embedded hardware to ensure seamless integration into clinical practice. Edge computing frameworks and quantization techniques could be applied to reduce computational load without sacrificing diagnostic accuracy, making the AI-enhanced Raman spectroscopy diagnostic system 112 viable even in resource-constrained environments such as community clinics or mobile diagnostic units.

In summary, the AI component of this Raman-based diagnostic platform was engineered with attention to clinical applicability, data variability, and interpretability. The integration of real-time performance, spectral sensitivity, personalized prediction, and clinician-facing transparency positions this AI system are focused on early detection and management of glaucoma and other eye diseases.

DETAILED DESCRIPTION OF SEVERAL
EMBODIMENTS

One innovation in this AI-enhanced Raman spectroscopy diagnostic system 112 lies in the integration of an artificial intelligence engine 202 tailored specifically for the detection and classification of glaucomatous changes. Traditional approaches to glaucoma diagnosis rely heavily on structural imaging and tonometry, often missing early biochemical cues that precede visual field loss. By leveraging Raman spectroscopy, the disclosed AI-enhanced Raman spectroscopy diagnostic system 112 detects molecular alterations at the site of aqueous humor 138 drainage, enabling pre-symptomatic diagnosis.

What distinguishes this platform is the use of an AI/ML interpretation model 134 trained on spectral datasets from diverse clinical populations. The AI/ML interpretation model 134 identifies biomolecular patterns characteristic of glaucoma and is capable of differentiating between various stages of the disease. It employs neural networks for pattern recognition and incorporates longitudinal data to enhance predictive accuracy. Furthermore, its explainability module 204 ensures that clinicians can interpret AI-generated results with transparency, addressing a common limitation in black-box algorithms.

The capacity of the AI-enhanced Raman spectroscopy diagnostic system 112 to adapt to individual patient profiles enhances both its diagnostic and prognostic capabilities. By updating its classification thresholds over time based on patient-specific responses, it becomes a dynamic tool for monitoring disease progression and therapeutic efficacy. The artificial intelligence engine 202 operates in real time, allowing immediate integration into clinical workflows without delaying the diagnostic process.

Some embodiments of the disclosed AI-enhanced Raman spectroscopy diagnostic system 112 relate to a Raman spectroscopy-based diagnostic platform enhanced by artificial intelligence, configured to detect and interpret biomolecular signatures in the aqueous humor 138 of the anterior chamber of the eye 102.

Intraocular Pressure (IOP) Linked Biomarkers

In a disease-free state, the aqueous humor 138 contains a physiologically stable composition of proteins, cytokines, antioxidants, and metabolites, each of which exhibits characteristic Raman spectral features. The aqueous humor 138 contains a complex mix of molecules that reflect normal physiological activity, homeostasis, and baseline immune surveillance. The system's AI/ML interpretation model 134 is trained to recognize this baseline spectral profile, enabling it to distinguish between normal molecular presence and disease-associated biomarker elevation, structural modification, or accumulation.

TABLE 2

Confidence Estimation in Medical AI

Bayesian Neural Networks with Confidence Estimations: This study explores the application of Bayesian neural networks in medical diagnostics, emphasizing the importance of confidence estimates in clinical decision-making. Citation: O'Hagan, A. (1999). Bayesian neural networks with confidence estimations applied to data mining. Computational Statistics & Data Analysis, 30(1), 99-122. Artificial Intelligence with Statistical Confidence Scores for Detection: This research discusses the implementation of AI systems that provide statistical confidence scores, enhancing the reliability of medical diagnoses. Citation: Chilamkurthy, S., Ghosh, R., Tanamala, S., Biviji, M., Campeau, N.G., Venugopal, V.K., Mahajan, V., Rao, P., & Warier, P. (2018). Deep learning algorithms for detection of critical findings in head CT scans: a retrospective study. The Lancet, 392(10162), 2388-2396. Application of Uncertainty Quantification to Artificial Intelligence in Medicine: This article highlights the significance of uncertainty estimation in AI models to improve safety and efficacy in healthcare applications. Citation: Begoli, E., Bhattacharya, T., & Kusnezov, D. (2019). The need for uncertainty quantification in machine-assisted medical decision making. Nature Machine Intelligence, 1(1), 20-23. Bayesian Convolutional Neural Networks in Medical Imaging: This work demonstrates how Bayesian CNNs can address data scarcity challenges in medical imaging by providing confidence estimates, thereby increasing model reliability. Citation: Kendall, A., & Gal, Y. (2017). What uncertainties do we need in Bayesian deep learning for computer vision? In Advances in Neural Information Processing Systems (pp. 5574-5584).

For example, molecules such as TGF-β2 and VEGF are present in trace amounts under normal conditions but exhibit distinct Raman signal amplification or peak shifting in pathological states such as glaucoma or intraocular neoplasia. Similarly, metabolic markers like lactate and glutathione maintain narrow spectral baselines in health but shift in response to hypoxia or oxidative stress.

TABLE 3

Key Biomarker Classes in Normal Aqueous Humor

| Type | Examples | Purpose in Normal Eye |
|---|---|---|
| Proteins | Albumin, transferrin, alpha-crystallin | Nutrient transport, antioxidant function |
| Cytokines (very low levels) | IL-6, TGF-β2 | Immune privilege, suppression of inflammation |
| Enzymes | Carbonic anhydrase, glutathione peroxidase | Metabolic regulation, redox balance |
| Growth Factors | VEGF (very low), bFGF | Basal support of vascular tone, cell maintenance |

TABLE 3-continued

Key Biomarker Classes in Normal Aqueous Humor

| Type | Examples | Purpose in Normal Eye |
|---|---|---|
| Metabolites | Lactate, glucose, ascorbic acid | Energy metabolism, antioxidant protection |
| Lipoproteins & small lipids | HDL-like particles, cholesterol | Membrane maintenance, signaling |
| Extracellular vesicles (low quantities) | Microvesicles, exosomes | Intercellular signaling and waste transport |

The AI-enhanced Raman spectroscopy diagnostic system 112 applies adaptive spectral normalization and pattern recognition algorithms to compare real-time data against validated reference spectra, ensuring accurate differentiation between normal physiological variation and clinically relevant biomarker expression.

The disclosed AI-enhanced Raman spectroscopy diagnostic system 112 can compare elevated or shifted signals with the normal spectral background. Some normal molecules become disease biomarkers only when their concentrations rise or their chemical structures change. Examples include: TGF-β2 is normal in small amounts but elevated in glaucoma and VEGF, which is low in normal eyes but elevated in uveitis, diabetic retinopathy, or tumors. In many cases, there is a correlation between intraocular pressure (IOP) and both the quantity and spectral characteristics of specific biomarkers in the aqueous humor 138. The strength and nature of the correlation depends on the biomarker in question, underlying pathophysiology (e.g., mechanical strain, hypoxia, inflammation), and whether measurements are associated with acute, chronic, or compensated IOP elevation.

The disclosed AI-enhanced Raman spectroscopy diagnostic system 112 further supports the assessment of intraocular pressure through the molecular analysis of Raman spectral data, offering a biochemical complement to conventional mechanical tonometry. The disclosed AI-enhanced Raman spectroscopy diagnostic system 112 takes into account baseline Raman spectrums, even in healthy eyes 102, and an AI/ML interpretation model 134 that is trained to distinguish physiological baseline from disease-associated shifts. The disclosed AI-enhanced Raman spectroscopy diagnostic system 112 also has detection thresholds that must be carefully calibrated to avoid false positives from normal fluctuations.

One key insight lies in the quantitative correlation between biomarker concentration and Raman spectral intensity. As the concentration of a given biomolecule—such as transforming growth factor beta-2 (TGF-B2-β2)—increases in the aqueous humor 138, the corresponding Raman peaks become more prominent. This concentration-dependent intensification provides a foundation for semi-quantitative analysis, enabling the AI-enhanced Raman spectroscopy diagnostic system 112 to infer the biochemical burden associated with elevated IOP. Thus, the AI-enhanced Raman spectroscopy diagnostic system 112 not only identifies the presence of disease-related molecules but may also gauge their relative abundance in a physiologically meaningful context.

Beyond concentration alone, Raman spectroscopy captures spectral features that reflect molecular structure and interactions. Structural changes in biomolecules, including oxidation, crosslinking, or protein aggregation, may induce shifts in Raman peak position or broaden their shape—subtleties that do not necessarily depend on concentration.

These spectral alterations may reflect oxidative stress or conformational modifications associated with chronically elevated IOP. The artificial intelligence engine 202 within the AI-enhanced Raman spectroscopy diagnostic system 112 is trained to recognize these nuanced spectral patterns, allowing it to detect molecular stress responses that precede or accompany glaucomatous damage.

Expanding beyond individual molecular markers, the AI-enhanced Raman spectroscopy diagnostic system 112 is also capable of identifying composite spectral signatures indicative of IOP-related physiological changes. Rather than relying on a single biomarker, the AI/ML interpretation model 134 can learn to associate patterns across multiple spectral bands—encompassing proteins, lipids, and metabolites—with elevated IOP states. This multimodal IOP signature allows the AI-enhanced Raman spectroscopy diagnostic system 112 to produce a more holistic biochemical assessment, offering a novel complement to traditional pressure-based measurements. Such an approach strengthens the diagnostic utility of the AI-enhanced Raman spectroscopy diagnostic system 112, especially in cases where mechanical tonometry may be inconclusive or compromised by corneal biomechanics or patient compliance.

TABLE 4

Normal Biomarkers in Disease-Free Aqueous Humor and Their
Functional Correlates with Intraocular Pressure (IOP)

| Biomarker | Type | Function/Role | Typical Presence in Healthy Eyes |
|---|---|---|---|
| Ascorbic Acid (Vitamin C) | Antioxidant | Scavenges free radicals; protects ocular tissues | High concentration |
| Glucose | Metabolite | Energy substrate | Present in low but stable amounts |
| Lactate | Metabolite | Byproduct of glycolysis | Detectable under aerobic and anaerobic conditions |
| Albumin | Protein (Transport) | Maintains osmotic pressure; transports molecules | Low concentration |
| Transferrin | Protein (Iron-binding) | Iron transport and homeostasis | Present at trace levels |
| Urea | Waste metabolite | Diffuses from plasma | Present in small amounts |
| Cystatin C | Proteinase inhibitor | Protects against enzymatic tissue degradation | Low levels |
| Electrolytes (Na+, K+, Cl−, Ca2+) | Inorganic ions | Maintain aqueous humor osmolality and function | Normal physiologic levels |
| Hyaluronic Acid (trace) | Glycosamino-glycan | Contributes to viscoelastic properties | Present in trace quantities |
| Immunoglobulin A (IgA) | Immune protein | First-line mucosal immunity | Trace levels; Contributes to ocular immune privilege |

Clinical Use Scenarios

In a typical clinical scenario, a patient undergoing routine screening may be examined with the mounted Raman spectroscopy probe 142 during a slit lamp evaluation. The Raman spectroscopy probe 142 captures aqueous humor 138 spectra in less than five seconds, and the artificial intelligence engine 202 renders a result within ten seconds. If the AI-enhanced Raman spectroscopy diagnostic system 112 detects a biomarker profile consistent with early glaucomatous stress—such as elevated 8-OHdG combined with reduced MMP activity—the software may recommend additional testing or immediate referral, even if IOP and OCT findings are within normal limits.

Alternatively, for a patient with known uveitis, the AI-enhanced Raman spectroscopy diagnostic system 112 may detect inflammatory signatures—such as interleukin-6 or TNF-α—during remission, indicating subclinical disease activity. Such detection could support decisions regarding tapering or intensifying immunosuppressive therapy.

The modularity of the AI-enhanced Raman spectroscopy diagnostic system 112 also allows for updates: as new ocular biomarkers are discovered and their Raman shifts validated, the artificial intelligence engine 202 can be retrained to include additional diagnostic categories. The AI-enhanced Raman spectroscopy diagnostic system 112 is also compatible with cloud-based learning models, enabling remote diagnostics and population-wide data aggregation for continuous improvement.

Illustrative Clinical Scenario: TGF-B2 Elevation and High IOP With Normal Optic Nerve Imaging Clinical Context: A 57-year-old patient presents for a routine eye examination. They are asymptomatic, with 20/20 visual acuity in both eyes. However, applanation tonometry reveals elevated intraocular pressure—26 mmHg OD and 25 mmHg OS—on two separate visits. Gonioscopy shows open angles bilaterally, and central corneal thickness is within normal limits. The optic nerve appears healthy on fundoscopy, with a cup-to-disc ratio of 0.3 bilaterally, and OCT retinal nerve fiber layer (RNFL) analysis shows no significant thinning. Visual field testing for each eye is normal.

Diagnostic Challenge: The elevated IOP suggests possible early glaucoma, but there is no structural or functional evidence of optic nerve damage at this stage. Conventional decision-making would involve periodic observation or initiating empiric treatment.

Use of the AI-enhanced Raman spectroscopy diagnostic system 112: To guide management, the clinician performs a non-invasive Raman spectroscopy scan of the anterior chamber using the AI-enhanced Raman spectroscopy diagnostic system 112. The scan detects a significantly elevated concentration of TGF-β2, a biomarker known to increase aqueous outflow resistance via extracellular matrix remodeling in the trabecular meshwork. The system provides the following output:

Biomarker Detected: TGF-β2.

Estimated Concentration: 92 pg/mL (normal reference: <45 pg/mL)

Diagnostic Flag: Elevated IOP-correlated biomarker pattern

Interpretation: Biochemical signature consistent with early molecular changes in ocular hypertension AI Contextual Interpretation: Despite normal imaging, the elevated TGF-β2 level and corresponding Raman peak intensity suggest that biochemical pathways associated with glaucomatous damage are already active, even if structural changes are not yet detectable. The AI-enhanced Raman spectroscopy diagnostic system 112 provides a moderate risk classification for glaucoma progression and recommends closer monitoring or initiation of pressure-lowering therapy.

Clinical Outcome: Based on the molecular evidence and the patient's IOP level, the clinician initiates treatment with a prostaglandin analog. Follow-up at 3 months shows IOP reduction to 18 mmHg, and repeat Raman spectroscopy demonstrates normalized TGF-β2 levels, correlating with improved outflow function.

In summary, this embodiment enables non-invasive, real-time, molecular diagnosis of anterior chamber pathologies by integrating AI analytics with Raman spectroscopy in a clinically operable form factor. It bridges the gap between molecular ophthalmology and practical diagnostics by delivering actionable insights at the point of care.

Illustrative Clinical Scenario: TGF-B2 Elevation in Uveitic Glaucoma

Clinical Context: A 45-year-old woman with a 2-year history of non-granulomatous anterior uveitis presents for follow-up. She has been managed with intermittent topical corticosteroids (prednisolone acetate 1%) and is currently on a tapering regimen. At today's visit, IOP is elevated at 28 mmHg OD and 24 mmHg OS. Slit lamp examination reveals trace anterior chamber cell OD, no keratic precipitates, and a quiet vitreous.

Optic nerve evaluation shows a cup-to-disc ratio of 0.5 OD and 0.4 OS, stable from prior visits. OCT reveals borderline RNFL thinning in the superior quadrant OD but no progression over the last 6 months. The patient reports compliance with both corticosteroids and a pressure-lowering agent (brimonidine).

Diagnostic Uncertainty: The elevated IOP raises concern for uveitic glaucoma, but there is ambiguity regarding whether the elevation reflects active inflammation, steroid response, or chronic trabecular damage. Structural progression is equivocal.

Use of the AI-Assisted Raman Diagnostic System: A Raman spectroscopy scan is performed using the AI-enhanced system. The following key findings are reported:

Biomarker Detected: TGF-β2 (concentration: 103 pg/mL)

Pharmaceutical Detected: Prednisolone acetate (concentration: 82 ng/ml)

AI Interpretation: Elevated TGF-β2 consistent with trabecular fibrosis or steroid-induced outflow resistance. No IL-6 or TNF-α elevation noted.

Diagnostic Flag: Elevated IOP in pharmacologically suppressed uveitic eye; biochemical profile favors steroid-induced IOP elevation over active inflammatory glaucoma.

AI Contextual Inference: The absence of inflammatory biomarkers (e.g., IL-6, TNF-α) and the detection of therapeutic-range corticosteroids in combination with elevated TGF-β2 suggest a steroid-response mechanism as the primary driver of increased IOP. The artificial intelligence engine 202 adjusts its output accordingly, emphasizing controlled inflammation with treatment induced outflow dysfunction.

Clinical Response: The clinician discontinues the corticosteroid and initiates a non-steroidal anti-inflammatory agent. IOP normalizes within two weeks. Repeat Raman analysis confirms reduction in TGF-β2 concentration to 48 pg/mL and clearance of corticosteroid signal.

This scenario illustrates how the AI-assisted Raman diagnostic system not only distinguishes inflammation from steroid response, but also uses TGF-β2 as a surrogate marker for fibrotic trabecular changes-supporting precision-guided management of complex uveitic glaucoma cases.

Variable Factors Considered by AI-Assisted Raman Spectroscopy

Sampling Variability

In one embodiment, the Raman excitation beam from the laser 106 is aligned with the central optical axis and focused on the central anterior chamber of the eye 102. This location provides a practical, reproducible target for acquiring Raman spectral data representative of biomarker dispersion within the aqueous humor 138. The setup is compatible with slit-lamp-mounted or handheld Raman spectroscopy probe 142 configurations and may not require gonioscopic lenses or invasive positioning.

The AI/ML interpretation model 134 is trained on data from the central chamber and uses advanced spectral processing to detect disease-relevant molecular signatures. This includes identifying spectral patterns even when biomarker levels are diluted or influenced by systemic variables. Considerations regarding the limitations of central sampling are addressed in the accompanying table.

TABLE 5

| Sampling Caveats and Limitations | | |
|---|---|---|
| Consideration | Impact | Mitigation |
| Dilution effect | Peripheral-release biomarkers may appear at lower levels | Use signal averaging/ normalization |
| Transient concentration gradients | May miss acute, localized biomarker spikes (e.g., trauma) | Time-standardized sampling post-event |
| Larger or bound molecules | May diffuse more slowly | Target chronic rather than acute signatures |
| Non-diffusible vesicles | May be localized near release sites (e.g., exosomes) | Use peripheral scan mode as a secondary option |

The aqueous humor 138 functions as a dynamic, circulating medium, with continuous flow from the ciliary body and convection through the anterior chamber. As a result, biomarkers originating in peripheral tissues—including Schlemm's canal, trabecular meshwork, iris, and ciliary body—are generally dispersed into the central anterior chamber, where they are soluble.

Dispersion into the central anterior chamber enables overall aqueous biomarker levels throughout the anterior chamber, especially for soluble proteins (e.g., TGF-β2, VEGF, IL-6), oxidative markers (e.g., lactate, 8-isoprostane), metabolites, and small molecules. Consistent focusing at the center of the anterior chamber is sufficient for biomarker detection and for maintaining the consistency of methodology over sequential analysis.

Central axis targeting avoids the anatomical variability of the angle. In reality, it is more practical in real-world clinical settings; easier alignment, less discomfort, avoidance of special instrumentation on the surface of the eye 102 and faster scans. The artificial intelligence engine 202 can be trained to detect subtle variations in biomarker concentrations centrally, using patters, rations, or shifts. Even diluted biomarkers can be reliably classified with proper AI feature engineering.

In another embodiment, the AI-enhanced Raman spectroscopy diagnostic system 112 includes anatomical awareness by incorporating metadata on Raman spectroscopy probe 142 position and angle, or detecting spectral interference of the sampling region (e.g., central vs. peripheral characteristics). The confidence level of results is adjusted based on the historical reliability of biomarker expression by location and known diffusion models for the target biomarkers. See Table 6: Location-Based Reliability Estimation. If sampling was central but peripheral markers are expected, the system may annotate: "Centrally acquired spectrum. Peripheral biomarker reliability reduced."

TABLE 6

Location-Based Reliability for Biomarker Detection in the Anterior Chamber

| Anatomical Location | Reliability for Biomarker Detection | Best Suited Biomarkers | Justification |
|---|---|---|---|
| Central Aqueous Humor | ★★★★☆ (High) | Glucose, lactate, urea, ascorbic acid | Uniformly mixed fluid compartment; minimal structural interference |
| Peripheral Aqueous (near angle) | ★★★☆☆ (Moderate) | TGF-β2, IL-6, TIMP-1, fibronectin | Slight turbulence and diffusion gradient from adjacent structures |
| Anterior Surface of Iris | ★★☆☆☆ (Low) | Inflammatory cytokines, pigmentation-related proteins | Absorptive pigmentation interferes with signal; proximity to vasculature |
| Trabecular Meshwork | ★★★★★ (Very High) | MMPs, TIMPs, ECM-related markers | Local production site; structural proteins and ECM turnover biomarkers abundant |
| Schlemm's Canal (inner wall) | ★★★★☆ (High, with depth targeting) | Endothelial markers, nitric oxide synthase, VEGF | Biomarkers are wall-bound; requires lateral or confocal targeting |
| Corneal Endothelium | ★★★☆☆ (Moderate) | Cystatin C, Na$^+$/K$^+$ ATPase, carbonic anhydrase | Accessible and stable layer; useful for evaluating pump-related metabolic markers |
| Posterior Chamber/ behind iris | ★☆☆☆☆ (Very Low) | Not optically suited for Raman interrogation | Limited light penetration and difficult access with anterior probes |

In certain embodiments, the disclosed AI-assisted Raman diagnostic system improves diagnostic reliability through temporal averaging, time-aware normalization, and spectral feature-based anatomical inference. To account for circadian fluctuations in biomarker expression, such as diurnal variation in IL-6 or cortisol, the system applies time-aware normalization, a calibration process that adjusts spectral interpretation based on the time of day at which data is acquired. During a single scan session, multiple spectra may be collected and averaged to reduce stochastic noise and enhance signal fidelity. This approach increases classification confidence, particularly in the presence of ambient lighting variability or minor ocular motion.

Additionally, the AI/ML interpretation model 134 is trained to infer the approximate anatomical origin of a given spectrum-central vs. peripheral-based on signal shape, intensity, and feature distribution, even in the absence of explicit Raman spectroscopy probe 142 position metadata. This inferred location informs a context-adjusted confidence score, further supporting accurate, explainable diagnostic decision-making. See Table 5: Sampling Caveats and Limitations.

Confidence Score and Reliability Metrics

In order to ensure diagnostic accuracy and provide interpretable, trustworthy results, the disclosed AI-enhanced Raman spectroscopy diagnostic system 112 includes a confidence estimation framework grounded in two complementary approaches: signal-based confidence scoring and location-based reliability estimation.

TABLE 7

AI Pipeline with Confidence Estimation

A confidence estimation within the AI-driven Raman spectroscopy system for glaucoma detection
1. Spectral Data Acquisition: Raman spectra are collected from the patient's eye using the handheld or slit lamp-mounted probe.
2. Preprocessing: The raw spectral data undergo noise reduction, baseline correction, and normalization to ensure consistency.
3. Feature Extraction: A Convolutional Neural Network (CNN) analyzes the preprocessed spectra to identify pertinent molecular features indicative of glaucomatous changes.
4. Confidence Estimation Module:
    Utilizes Monte Carlo Dropout during inference to perform multiple stochastic forward passes. Calculates the mean and variance of these passes to derive a confidence score accompanying the diagnosis.
5. Risk Stratification: Based on extracted features and confidence scores, the system classifies the patient's glaucoma risk level (e.g., Low, Moderate, High).
6. Diagnostic Output: The final diagnosis is presented to the clinician, highlighting both the risk level and the associated confidence score, ensuring informed decision-making.

The signal-based confidence score focuses on the intrinsic quality of the Raman spectrum obtained from the sampled location. During each scan, the AI-enhanced Raman spectroscopy diagnostic system 112 evaluates a range of factors that impact signal integrity, including the signal-to-noise ratio (SNR), baseline flatness, peak clarity, and the completeness of the spectral profile. The AI/ML interpretation model 134 processes these features in real time to generate a confidence score-typically expressed as a normalized value between 0 and 1, or as a percentage from 0% to 100%. This score reflects whether key Raman peak regions are present and well-formed, whether the overall intensity exceeds minimum detection thresholds, and whether any motion, blinking, or environmental noise artifacts have degraded the data. If the confidence score falls below a predefined threshold, the AI-enhanced Raman spectroscopy diagnostic system 112 alerts the operator that the scan quality is suboptimal due to misalignment, improper focus, or transient eye 102 movement. This capability supports immediate rescanning and improves reliability in point-of-care settings.

In addition to intrinsic signal quality, the AI-enhanced Raman spectroscopy diagnostic system 112 accounts for anatomical context through location-based reliability estimation. Raman spectra acquired from the anterior chamber may vary depending on whether the beam is directed centrally or toward peripheral regions such as the iridocorneal angle. The AI/ML interpretation models 134 are trained to recognize how spectral patterns differ across these locations and to associate each anatomical zone with a corresponding reliability modifier. This estimation is informed by either explicit metadata—such as Raman spectroscopy probe 142 angle or a location tag—or by inferring the sampling location directly from the spectral shape and feature distribution.

The AI-enhanced Raman spectroscopy diagnostic system 112 uses known diffusion dynamics and historical biomarker data to assess the likelihood that meaningful molecular signals are present in a given region. For example, centrally acquired spectra may offer reliable detection of soluble biomarkers, while scans aimed toward the angle may be less consistent due to anatomic variability and lower molecular dispersion. This allows the system to annotate results accordingly, such as stating: "Reading acquired centrally; reliability for angle-localized biomarkers reduced."

Together, these signal- and location-aware scoring mechanisms help guide clinical interpretation, enhance transparency in AI outputs, and support quality assurance for Raman-based diagnostics in ophthalmic applications.

The artificial intelligence engine 202 of the disclosed AI-enhanced Raman spectroscopy diagnostic system 112 is further configured to provide a reliability metric for each scan, including signal strength and location, based on one or more of the following: (1) intrinsic spectral signal quality, (2) anatomical sampling location, (3) predictive model variance, and (4) inter-model consensus. This reliability metric is output alongside the diagnostic interpretation and may be expressed as a confidence value or as a categorical quality grade (e.g., High, Moderate, and Low). The reliability score assists clinicians in determining whether a rescan is necessary or whether the data are sufficient for diagnostic use.

AI-Raman Synchronization

To address this, the AI architecture is designed with modular components that can be independently updated and synchronized with changes in the Raman acquisition platform. For instance:

Spectral Calibration Modules are updated to reflect revised baseline behaviors or extended wavenumber detection ranges.

Preprocessing Pipelines are retrained to denoise or normalize spectra acquired under different optical conditions.

Biomarker Signature Libraries are expanded to reflect improvements in detection sensitivity or resolution for certain Raman peaks.

Hardware Metadata Parsers allow the AI to adjust its expectations dynamically based on the specific spectrometer 116 model or software version in use.

These updates are governed by a robust version control and validation framework to ensure traceability, consistency, and compliance with regulatory standards. The AI update, whether initiated due to data drift, biomarker discovery, or Raman hardware modification, may be accompanied by performance benchmarking, regression testing, and documentation.

Differential Biomarker Signatures in the Trabecular Meshwork and Schlemm'S Canal: Implications for AI-Enhanced Raman Diagnostics The anterior chamber angle of the eye 102 is home to two structurally adjacent yet biologically distinct tissues that play a central role in intraocular pressure (IOP) regulation: the trabecular meshwork (TM) and Schlemm's canal (SC). While functionally integrated in facilitating aqueous humor 138 outflow, these structures differ significantly in their cellular composition, molecular behavior, and associated biomarker signatures. Understanding these distinctions is useful for accurate interpretation of Raman spectral data, especially when processed through an AI-assisted diagnostic system.

The trabecular meshwork is composed of a porous, collagen-rich network lined with specialized cells that share some endothelial characteristics but are primarily fibroblast-like in nature. These trabecular cells are highly responsive to mechanical stimuli and actively modulate extracellular matrix (ECM) turnover, maintaining tissue homeostasis and modulating outflow resistance. trabecular meshwork-derived biomarkers often reflect matrix remodeling, fibrosis, and oxidative stress. Common examples include:

TGF-β isoforms (especially TGF-β2)-associated with fibrotic responses and ECM deposition MMP-9 and other matrix metalloproteinases—enzymes involved in matrix breakdown TIMPs (tissue inhibitors of metalloproteinases)—regulators of MMP activity Fibronectin, laminin, and collagen IV—structural ECM components elevated in TM pathology 8-OHdG (8-hydroxy-2'-deoxyguanosine)—a marker of oxidative DNA damage Myocilin—a protein linked to TM dysfunction and familial forms of glaucoma By contrast, Schlemm's canal is a true vascular endothelium, more analogous to lymphatic and venous structures. Its endothelial cells form a monolayer with tight junctions and express classical vascular markers such as:

VE-cadherin, PECAM-1 (CD31), and Prox1—markers of endothelial identity and permeability ICAM-1 and IL-6—indicative of inflammatory activation and endothelial stress VEGF (vascular endothelial growth factor)—involved in angiogenic signaling and barrier modulation Nitric oxide synthase (NOS)—reflecting vascular tone and endothelial response to shear stress These Schlemm's canal-derived biomarkers are typically associated with mechanotransduction, inflammatory signaling, and endothelial integrity. Of particular note, Schlemm's canal endothelial cells are exquisitely sensitive to changes in shear stress and intraocular pressure, and their biomarker profile may shift dramatically under pathological loading conditions.

While both the trabecular meshwork and Schlemm's canal contribute molecular content to the aqueous humor 138, their biomarkers differ in origin, abundance, and clinical interpretation. Trabecular meshwork biomarkers typically suggest fibrotic, mechanical, or oxidative etiologies, while Schlemm's canal biomarkers often reflect vascular, inflammatory, or permeability-related processes.

TABLE 8

| Stressors Triggering Biomarker Release from the Trabecular Meshwork | | |
|---|---|---|
| Stressor or Condition | Mechanism | Associated Biomarkers |
| Mechanical strain/ elevated IOP | Stretching and deformation of TM cells activates remodeling pathways | TGF-β2, MMP-2, MMP-9, TIMPs, fibronectin |
| Oxidative stress | Reactive oxygen species (ROS) damage cellular components | 8-OHdG, malondialdehyde (MDA), reduced glutathione |
| Aging and senescence | Alters ECM turnover, increases stiffness and biomarker expression | Myocilin, LOXL1, TGF-β1/β2 |
| ECM accumulation or fibrosis | Excessive ECM deposition induces compensatory enzymatic remodeling | Collagen IV fragments, tenascin-C, laminin fragments |

TABLE 9

| Stressors Triggering Biomarker Release from Schlemm's Canal | | |
|---|---|---|
| Stressor or Condition | Mechanism | Associated Biomarkers |
| Shear stress/ elevated IOP | Distorts SC endothelial cells and alters tight junction integrity | ICAM-1, VE-cadherin, nitric oxide synthase (NOS), IL-6 |
| Endothelial barrier disruption | Damage to cell junctions or pore formation permits diffusion of inflammatory mediators | VEGF, IL-8, MCP-1, PECAM-1 |
| Inflammatory microenvironment | Cytokines induce SC endothelial activation and leukocyte recruitment | IL-1β, TNF-α, ICAM-1, CXCL12 |
| Immune-mediated injury/ uveitis | Systemic or intraocular inflammation affects SC lining | IL-6, VEGF, soluble adhesion molecules |
| Ischemia or altered perfusion pressure | Vascular stress alters SC endothelial metabolism | NO (nitric oxide), HIF-1α, endothelin-1 |
| Pharmacological modulation of endothelial phenotype | Steroids or prostaglandins alter barrier function or promote fibrosis | TGF-β2, endothelin, CD31 modulation |

The AI-assisted Raman diagnostic system is specifically configured to leverage this anatomical specificity. Using contextual inference algorithms, it interprets spectral features in relation to both molecular identity and likely tissue origin. For instance:

Elevated TGF-β2 and MMP-9 may indicate trabecular meshwork-associated ECM remodeling and fibrosis.

Concurrent elevation of ICAM-1 and IL-6 may point toward Schlemm's canal endothelial activation or dysfunction.

The spectrometer 116 sends spectral data in digital format to the computer 118. The one or more processors 124 of the computer 118 then use the artificial intelligence engine 202 to analyze the spectral signature and detect molecular features indicative of melanin, protein, or lipid content—biomarkers associated with intraocular anomalies 104. The artificial intelligence engine 202 interprets the data and transmits the diagnostic output, including classification results, molecular probabilities, and other indicators, to a user interface 132 for clinical review.

The distinctions between trabecular meshwork and Schlemm's canal pathology carry direct therapeutic implications. When dysfunction of the trabecular meshwork is identified, the AI-enhanced Raman spectroscopy diagnostic system 112 may suggest antifibrotic or matrix-modulating therapeutic strategies. In contrast, when endothelial dysfunction of Schlemm's canal predominates, the diagnostic output of the artificial intelligence engine 202 may indicate the need for anti-inflammatory or endothelial-targeted therapy. This stratified diagnostic capability is particularly valuable in early-stage or diagnostically complex cases of glaucoma, such as uveitic glaucoma, where inflammation may initially affect Schlemm's canal, or in primary open-angle glaucoma, where early remodeling of the trabecular meshwork may precede detectable structural changes on conventional imaging.

Accordingly, while the trabecular meshwork and Schlemm's canal operate together in maintaining intraocular pressure homeostasis, they are anatomically and molecularly distinct. Incorporating this distinction into AI-driven Raman analysis enhances diagnostic precision, facilitates targeted therapeutic recommendations, and aligns with the goals of personalized, predictive, and molecularly informed ophthalmic care.

TABLE 10

| Comparative of Biomarkers: Trabecular Meshwork vs. Schlemm's Canal | | |
|---|---|---|
| Biological Feature | Trabecular Meshwork (TM) | Schlemm's Canal (SC) |
| Cell Type | Specialized connective tissue cells with some endothelial-like features | True endothelial cells |
| Function | Regulates aqueous outflow resistance; ECM remodeling | Collects and transports aqueous humor to episcleral veins |
| Mechanical Sensitivity | Responsive to mechanical stretch, pressure | Responsive to shear stress from aqueous flow |
| Inflammatory Markers | Elevated IL-1, TNF-α, MMPs in glaucoma | Elevated IL-6, ICAM-1 under stress or injury |
| Oxidative Stress Markers | 8-OHdG, glutathione alterations | 8-isoprostane, increased ROS response |
| ECM Components | Fibronectin, collagen IV, laminin, MMPs, TIMPs | Low ECM deposition; ICAM-1 expression |
| Unique Markers | Myocilin (in response to steroids), LOXL1 | PECAM-1, VE-cadherin |
| Pharmacologic Response | Modulates outflow resistance to ROCK inhibitors, steroids | Sensitive to agents affecting junctional integrity |

Early Detection of Glaucomatous Stress Via Biomarker Profiling By AI-Assisted Raman Spectroscopy The pathogenesis of glaucoma unfolds gradually, often beginning at the molecular level before manifesting any structural abnormalities detectable through imaging modalities like Optical Coherence Tomography 136 (OCT). Central to this early cascade are biochemical stress signals released by the trabecular meshwork (TM) and Schlemm's canal (SC) in response to pressure, inflammation, oxidative damage, or mechanical strain.

Even in the preclinical stage, when visual function and retinal architecture appear normal, cells within the TM and SC can begin secreting stress biomarkers such as transforming growth factor-beta 2 (TGF-β2), matrix metalloproteinase-9 (MMP-9), interleukin-6 (IL-6), intercellular adhesion molecule-1 (ICAM-1), and 8-hydroxy-2'-deoxyguanosine (8-OHdG). These molecular signals may be detectable within hours to days of an inciting event, long before the development of ganglion cell loss or retinal nerve fiber layer (RNFL) thinning observed on OCT.

This temporal disconnect offers a powerful diagnostic opportunity. By using AI-assisted Raman spectroscopy, these subtle yet biologically meaningful changes in the aqueous humor 138 can be non-invasively detected and interpreted in real time. The AI/ML interpretation model 134 not only recognizes spectral peaks associated with each biomarker but also interprets their elevation within clinical context, distinguishing early molecular disturbance from established structural damage.

TABLE 11

| Timeline of Biomarker Detection vs. Structural Change | | |
|---|---|---|
| Disease Phase | Biomarker Activity | OCT Findings |
| Preclinical/Pre-symptomatic | Early elevation in TGF-β2, IL-6, ICAM-1, 8-OHdG, MMP-9 | No change-optic nerve and RNFL normal |
| Early functional disturbance | Biomarkers persist or intensify, ECM remodeling begins in TM | Subtle or no OCT change |
| Structural onset (visible on OCT) | Elevated biomarkers coincide with RNFL thinning and optic nerve head changes | Structural defects begin to appear |
| Advanced disease | Fibrosis-related biomarkers become predominate; oxidative stress and inflammation ongoing | Clear RNFL loss, visual field deterioration |

By leveraging this molecular timeline, the AI-assisted Raman diagnostic system provides a unique clinical advantage: it enables proactive glaucoma management rather than reactive treatment. In patients with normal intraocular pressure or ambiguous clinical findings, early biomarker signatures can offer decisive evidence of incipient pathology, guiding earlier intervention and closer monitoring.

In summary, the ability to detect aqueous humor 138 biomarkers ahead of structural degeneration redefines how glaucoma may be diagnosed and managed. It represents a shift from morphology-driven diagnosis to molecular-level, personalized screening, with the potential to preserve vision through earlier, targeted therapy.

Biomarkers, Structural Change, and Functional Loss in Glaucoma Diagnosis

In the progression of glaucomatous disease, functional impairment often lags behind underlying structural damage. Studies have shown that up to 30-50% of retinal ganglion cells (RGCs) may be lost before measurable changes appear on standard visual field testing. This delay is due in part to the visual system's functional reserve, which allows early neuronal loss to go undetected by visual field assessments.

Optical Coherence Tomography 136 (OCT) has significantly enhanced the clinician's ability to detect early structural changes, particularly thinning of the retinal nerve fiber layer (RNFL) and ganglion cell-inner plexiform layer (GCIPL). OCT offers a non-invasive and objective method to quantify the integrity of the inner retina, but even this high-resolution imaging technique identifies changes only after cellular damage has already occurred.

By contrast, biomarker analysis offers a window into even earlier stages of disease, before irreversible structural loss is evident. Cells under stress, such as those within the trabecular meshwork or Schlemm's canal, respond by altering their secretome, releasing distinct sets of molecules into the aqueous humor 138. These stress-induced biomarkers include:

TGF-β2, fibronectin, and MMP-9 in the setting of ECM remodeling and trabecular resistance, IL-6, ICAM-1, and VEGF in association with endothelial activation, inflammation, or hypoxic stress within Schlemm's canal.

These molecular signals can be detected in vivo via Raman spectroscopy, particularly when enhanced by artificial intelligence trained to recognize early, context-dependent spectral changes. Unlike OCT or visual field testing, which reflect downstream consequences of damage, biomarker detection reveals real-time, upstream biochemical shifts—providing a powerful early-warning system for impending glaucomatous injury.

This diagnostic hierarchy, from molecular signaling to structural loss to functional deficit, creates a compelling rationale for multimodal integration, with AI-assisted Raman biomarker analysis occupying the earliest point in the disease timeline. When deployed effectively, this approach can:

Identify high-risk patients before visual field damage occurs,

Distinguish between different mechanisms of outflow dysfunction (e.g., fibrotic trabecular meshwork vs. inflamed Schlemm's canal), Guide preemptive therapy tailored to the biochemical phenotype of disease, and Monitor subtle treatment responses that may not yet affect structure or function.

Integrating biomarker-based Raman analysis into the diagnostic workflow allows for earlier detection of glaucomatous stress at the molecular level, offering the potential to inform clinical decisions before structural or functional damage becomes apparent.

Diurnal Variation

Several ocular biomarkers exhibit diurnal variation, meaning their concentration in the aqueous humor 138 fluctuates throughout the day. This is especially relevant for the disclosed AI-enhanced Raman spectroscopy diagnostic system 112 for biomarkers, since time of day may affect the spectral profile and diagnostic interpretation.

TABLE 12

| Key Biomarkers with Known Diurnal Fluctuations | | |
|---|---|---|
| Biomarker | Diurnal Pattern | Clinical Relevance |
| Cortisol | Peaks in the early morning; declines by evening | Regulates intraocular pressure and inflammatory balance |
| Aqueous Humor pH | Slight diurnal shifts; more acidic in the morning | May alter Raman peak baselines |
| TGF-β2 | Reported circadian variation in animal models | Affects extracellular matrix and IOP regulation |
| Melatonin | Rises at night; low during day | Modulates IOP, immune activity, and aqueous secretion |
| Nitric Oxide (NO) | Varies with ocular perfusion and circadian rhythms | May affect trabecular meshwork outflow and IOP control |
| Endothelin-1 (ET-1) | Tends to increase at night in glaucoma patients | Vasoconstrictor; may impair optic nerve perfusion |
| IOP-linked oxidative markers | Lactate, ROS-related products may vary indirectly with IOP | Reflect metabolic stress during high-pressure periods |

To ensure consistent diagnostic accuracy, the disclosed AI-enhanced Raman spectroscopy diagnostic system 112 incorporates time-awareness into both data acquisition and AI analysis. Certain biomarkers present in the aqueous humor 138, including cortisol, nitric oxide, melatonin, and TGF-β2, are subject to diurnal variation, which may influence Raman spectral profiles.

The AI-enhanced Raman spectroscopy diagnostic system 112 records the exact time of data acquisition, and the artificial intelligence engine 202 references a time-calibrated baseline when interpreting spectral features. Alternatively, clinical protocols may specify a fixed window for scanning (e.g., 8:00-10:00 AM) to minimize inter-session variability due to circadian biomarker shifts. See FIG. 5.

This strategy enables more accurate detection of disease-related biomarker elevations by distinguishing them from physiological time-of-day changes. To address potential variability due to diurnal biomarker fluctuation, the system includes time-of-day normalization strategies based on known circadian expression patterns of aqueous biomarkers. This normalization allows for consistent interpretation of measurements collected at different times.

TABLE 13

Implications of Diurnal Variations for Raman Spectroscopy and AI

1. Spectral Baseline Shifts
   Even in healthy eyes, spectra may differ
   slightly between morning and afternoon due to
   biomarker level changes.
   AI must learn time-dependent normalization
   or interpret spectra relative to time-of-day
   baselines.
2. Time-Stamped Training
   Models should include metadata about time
   of scan to account for diurnal bias.
   AI can use this to weigh or adjust
   predictions accordingly.
3. Clinical Protocol Standardization
   For consistency, Raman scanning should ideally
   be done at a fixed time of day (e.g.,
   morning) in longitudinal monitoring.

Intraocular Pressure

In a disease-free state, the aqueous humor 138 contains a physiologically stable composition of proteins, cytokines, antioxidants, and metabolites, each of which exhibits characteristic Raman spectral features. The aqueous humor 138 contains a complex mix of molecules that reflect normal physiological activity, homeostasis, and baseline immune surveillance. The system's AI/ML interpretation model 134 is trained to recognize this baseline spectral profile, enabling it to distinguish between normal molecular presence and disease-associated biomarker elevation, structural modification, or accumulation. See Table 3: Normal Biomarkers in Disease-Free Aqueous Humor.

For example, molecules such as TGF-β2 and VEGF are present in trace amounts under normal conditions but exhibit distinct Raman signal amplification or peak shifting in pathological states such as glaucoma or intraocular neoplasia. Similarly, metabolic markers like lactate and glutathione maintain narrow spectral baselines in health but shift in response to hypoxia or oxidative stress.

The AI-enhanced Raman spectroscopy diagnostic system 112 applies adaptive spectral normalization and pattern recognition algorithms to compare real-time data against validated reference spectra, ensuring accurate differentiation between normal physiological variation and clinically relevant biomarker expression.

The disclosed AI-enhanced Raman spectroscopy diagnostic system 112 is configured to compare elevated or shifted Raman signals against a validated normative spectral background, allowing it to detect molecular deviations indicative of disease. Not all detected molecules are pathological in origin-some biomarkers are present at baseline under physiological conditions and only become clinically relevant when their concentrations increase or their molecular structures undergo specific transformations.

For example, transforming growth factor beta-2 (TGF-β2) is typically found in low concentrations in healthy eyes but is significantly elevated in glaucomatous conditions, where it contributes to extracellular matrix remodeling and trabecular meshwork dysfunction. Similarly, vascular endothelial growth factor (VEGF) exists at low baseline levels in normal ocular environments but rises sharply in pathological states such as uveitis, diabetic retinopathy, or ocular tumors, often as a response to ischemia or inflammation.

The AI-enhanced Raman spectroscopy diagnostic system 112 is also capable of correlating intraocular pressure (IOP) with both the concentration and spectral characteristics of specific biomarkers within the aqueous humor 138. This relationship is not uniform across all biomarkers; rather, it depends on the molecular identity, the underlying disease mechanism (e.g., mechanical strain, oxidative stress, inflammatory signaling), and the temporal profile of the IOP elevation—whether acute, chronic, or compensated.

By integrating Raman spectral data with contextual clinical variables, the artificial intelligence engine 202 can differentiate between normal physiological fluctuations and disease-associated molecular signatures. These interpretations are further supported by structured reference data, such as that summarized in FIG. 6, which delineates the characteristic responses of various biomarkers to different IOP states.

The disclosed AI-enhanced Raman spectroscopy diagnostic system 112 further supports the assessment of intraocular pressure (IOP) through the molecular analysis of Raman spectral data, offering a biochemical complement to conventional mechanical tonometry. The disclosed AI-assisted Raman diagnostic system takes into account baseline Raman spectrums, even in healthy eyes, and an AI model that is trained to distinguish physiological baseline from disease-associated shifts. The disclosed AI-enhanced Raman spectroscopy diagnostic system 112 also has detection thresholds that must be carefully calibrated to avoid false positives from normal fluctuations.

One key insight lies in the quantitative correlation between biomarker concentration and Raman spectral intensity. As the concentration of a given biomolecule, such as transforming growth factor beta-2 (TGF-B2-β2), increases in the aqueous humor 138, the corresponding Raman peaks become more prominent. This concentration-dependent intensification provides a foundation for semi-quantitative analysis, enabling the AI-enhanced Raman spectroscopy diagnostic system 112 to infer the biochemical burden associated with elevated IOP. Thus, the AI-enhanced Raman spectroscopy diagnostic system 112 not only identifies the presence of disease-related molecules but may also gauge their relative abundance in a physiologically meaningful context.

TABLE 14

| Biomarker | Role | Correlation with IOP |
|---|---|---|
| TGF-β2 | Fibrosis, ECM production in TM | Upregulated in glaucoma; promotes resistance to outflow |
| MMP-9 | ECM degradation enzyme | Upregulated under mechanical stress |
| TIMP-1 | Inhibits MMPs; shifts ECM balance toward deposition | Increased in fibrotic TM |
| IL-6 | Inflammatory cytokine | Upregulated in hypertensive and inflamed eyes |
| IL-1β | Pro-inflammatory mediator | Elevated in glaucomatous aqueous humor |
| Nitric Oxide (NO) | Endothelial mediator; vasodilator | Increases with shear stress on SC endothelium |
| Glutathione (GSH)* | Antioxidant; detoxifies ROS | Decreases with oxidative stress |
| Lactate | Glycolytic byproduct; reflects hypoxia | Elevated in ischemic and high-IOP eyes |
| Myocilin (MYOC) | ECM-related protein; misfolds under stress | Induced by steroids and oxidative stress |
| ANGPTL7 | Induces ECM-related genes and fibrotic changes | Highly upregulated in glaucomatous TM |
| CTGF | Downstream of TGF-β2; fibrosis promoter | Overexpressed in glaucomatous outflow tissues |
| Decorin | Binds TGF-β; modulates collagen fibrillogenesis | Dysregulation impairs ECM homeostasis |
| Aquaporin-1 (AQP1) | Regulates aqueous fluid movement | Altered in TM and ciliary epithelium in glaucoma |
| Periostin | Matricellular protein involved in fibrosis | Upregulated in glaucomatous optic nerve |
| TNF-α | Cytokine involved in apoptotic and inflammatory processes | Elevated in glaucomatous tissues |
| Endothelin-1 ET-1) | Vasoconstrictor; reduces perfusion to optic nerve head | Increased in aqueous of glaucoma patients |
| HSP27/HSP70 | Cellular stress-response proteins | Overexpressed under oxidative or mechanical strain |

Beyond concentration alone, Raman spectroscopy captures spectral features that reflect molecular structure and interactions. Structural changes in biomolecules, including oxidation, crosslinking, or protein aggregation, may induce shifts in Raman peak position or broaden their shape—subtleties that do not necessarily depend on concentration. These spectral alterations may reflect oxidative stress or conformational modifications associated with chronically elevated IOP. The artificial intelligence engine 202 within the AI-enhanced Raman spectroscopy diagnostic system 112 is trained to recognize these nuanced spectral patterns, allowing it to detect molecular stress responses that precede or accompany glaucomatous damage.

Expanding beyond individual molecular markers, the AI-enhanced Raman spectroscopy diagnostic system 112 is also capable of identifying composite spectral signatures indicative of IOP-related physiological changes. Rather than relying on a single biomarker, the AI/ML interpretation model 134 can learn to associate patterns across multiple spectral bands—encompassing proteins, lipids, and metabolites—with elevated IOP states. This multimodal IOP signature allows the AI-enhanced Raman spectroscopy diagnostic system 112 to produce a more holistic biochemical assessment, offering a novel complement to traditional pressure-based measurements. Such an approach strengthens the diagnostic utility of the AI-enhanced Raman spectroscopy diagnostic system 112, especially in cases where mechanical tonometry may be inconclusive or compromised by corneal biomechanics or patient compliance.

Variables in Raman Spectral Analysis from Medications

Both Topical and Systemic Medications can Influence Biomarker Levels in the Aqueous humor, which in turn affects Raman spectral patterns.

TABLE 15

| | How Medications Alter Raman-Detectable Biomarkers | |
|---|---|---|
| Medicine Type | Examples | Effect on Biomarkers/Spectra |
| Topical IOP-lowering drops | Prostaglandin analogs, beta blockers | Alter NO signaling, cytokine levels, oxidative stress markers |
| Topical steroids/ NSAIDS | Prednisolone, ketorolac | Suppress inflammatory markers (IL-6, TNF-α) in aqueous humor |
| Systemic medications | Acetazolamide, antihypertensives | Influence metabolic markers, aqueous pH, electrolyte balance |
| Systemic anti-inflammatory | Steroids, biologics | Reduce cytokine-driven spectral signatures |
| Oral supplements | Antioxidants, omega-3s | Alter redox-related markers (e.g., glutathione, lipid oxidation) |

For the AI-enhanced Raman spectroscopy diagnostic system 112 to remain accurate and clinically robust, it must be configured to account for medication-related variables in one or more of the following ways:

TABLE 16

AI Configuration Strategies to Account for Medication Use

1. Medication Metadata Input
During patient setup, the system includes an input module for current medication list, dosage, and regimen.
AI model uses this as a feature to adjust classification thresholds or suppress false positives.
Example: If a patient is on topical steroids, the AI expects IL-6 to be suppressed, and won't flag its absence as a false negative.
2. Medication-Aware Model Branching
Models are trained on subgroups of spectra: medicated vs. unmedicated.
At runtime, the AI selects the appropriate model branch based on reported medication status.
3. Anomaly Flagging
If expected biomarker behavior does not align with known medication effects, the AI may flag the result as medication-affected, ambiguous, or requires clinical correlation.
4. Time-Since-Medication Adjustment
Advanced systems can include dose timing (e.g., "last drop 3 hrs ago") to estimate pharmacodynamic effects on biomarkers.

The artificial intelligence engine 202 is configured to account for the potential influence of topical and systemic medications on biomarker expression in the anterior chamber. Patient medication data may be manually entered or obtained from electronic medical records and is used as an input feature in the diagnostic model. The AI-enhanced Raman spectroscopy diagnostic system 112 adjusts its interpretation of Raman spectral features based on known effects of medications on cytokine expression, oxidative stress markers, and metabolic byproducts. This approach improves diagnostic accuracy and reduces false-negative or false-positive results associated with pharmacologic suppression or enhancement of aqueous biomarkers.

The ability to report a statistically meaningful confidence value not only aids in clinical decision-making but also provides a mechanism for AI governance, auditability, and regulatory compliance in future clinical trials or FDA approval pathways.

In certain embodiments, the disclosed AI-enhanced Raman spectroscopy diagnostic system 112 is further configured to detect, analyze, and quantify pharmacologic agents present in the aqueous humor 138 of the anterior chamber of the eye 102. These agents may include, but are not limited to, therapeutic compounds commonly used in the management of glaucoma and other ocular conditions.

This capability supports real-time therapeutic monitoring, assessment of treatment adherence, pharmacokinetic analysis, and detection of residual or interacting compounds. Furthermore, this embodiment integrates Raman-active drug detection with artificial intelligence-based classification and concentration estimation tailored to real-time intraocular use.

In one embodiment of the inventions, the disclosed AI-enhanced Raman spectroscopy diagnostic system 112 is equipped with an integrated pharmacologic detection module 212 designed to analyze the presence of drugs within the anterior chamber. This capability enhances diagnostic value by enabling the AI-enhanced Raman spectroscopy diagnostic system 112 not only to detect disease biomarkers, but also to evaluate the ocular pharmacokinetics of therapeutically applied agents.

The AI-enhanced Raman spectroscopy diagnostic system 112 utilizes a Raman spectroscopy probe 142, perhaps including the laser 106, beam splitter 108, charge-coupled device 110, and spectrometer 116, positioned along the central optical axis of the eye 102 to acquire spectral data directly from the aqueous humor 138. The Raman spectroscopy probe 142 operates at a laser wavelength within a safe ophthalmic range, typically centered around 785 nm, and collects Raman-shifted light within a bandwidth of approximately 400 to 1800 $cm^{-1}$ This spectral window captures the vibrational signatures of most small-molecule drugs commonly used in ophthalmology, particularly those targeting intraocular pressure, inflammation, and neuroprotection.

In some embodiments, the Raman spectroscopy probe 142 is placed in direct contact with the eye 102. The embodiment of a confocal probe with surface-enhancing substrates (SERS) that touches an anesthetized cornea is may be useful in both the aqueous and ocular tumor patent applications. The AI-enhanced Raman spectroscopy diagnostic system 112 described herein may include either a confocal optics with or without SERS. Confocal embodiments with SERS provide higher spatial resolution, allowing precise targeting of anatomical zones such as the trabecular meshwork or Schlemm's canal wall. Confocal configurations without SERS, in contrast, may offer improved simplicity and broader signal collection from dissolved biomarkers in the aqueous medium, particularly where precise depth isolation is not critical.

TABLE 17

Key Differences: Confocal vs. Non-Confocal SERS

| Feature | Confocal SERS Probe | Non-Confocal SERS Probe |
| --- | --- | --- |
| Depth resolution | High (selects focal plane) | Low (signal from all illuminated depths) |
| Spatial specificity | Excellent (good for targeting tissue layers) | Broad (bulk or surface fluid sampling |

TABLE 17-continued

| Key Differences: Confocal vs. Non-Confocal SERS | | |
| --- | --- | --- |
| Feature | Confocal SERS Probe | Non-Confocal SERS Probe |
| Optical complexity | Higher (requires pinholes, alignment) | Simpler and more compact |
| Sensitivity to interface | High-works well with transparent windows | High, especially with well-prepared surfaces |
| Use in aqueous humor | Ideal for targeting a layer (e.g., TM zone) | Effective for dissolved biomarker sampling |

Non-confocal SERS may improve the sampling of the aqueous humor 138 when sampling a well-mixed, fluid medium like aqueous humor 138 for glucose or drug molecules. Non-confocal SERS is helpful for broad biomarker capture, not precise layer-specific analysis. Non-confocal SERS is also useful when using fixed SERS-active substrates in the optical path (e.g., behind a sapphire window).

Once the Raman signal is collected, it is passed to a spectrometer 116 and computer 118 that includes an AI/ML interpretation model 134 trained on spectral datasets from known pharmacologic compounds. In some embodiments, the AI/ML interpretation model 134 and pharmacologic detection module 212 have been developed using supervised learning techniques, allowing it to detect and distinguish spectral peaks corresponding to drugs such as prostaglandin analogs (e.g., latanoprost), beta-blockers (e.g., timolol), carbonic anhydrase inhibitors (e.g., dorzolamide), alpha-2 agonists (e.g., brimonidine), and corticosteroids (e.g., prednisolone acetate). The spectral data undergoes preprocessing including baseline correction, noise filtering, and normalization before being analyzed by the AI/ML interpretation model 134 and pharmacologic detection module 212.

Upon identifying spectral patterns that match a known drug signature, the AI-enhanced Raman spectroscopy diagnostic system 112 proceeds to estimate the concentration of the compound in the concentration estimation module 206. This estimation is carried out using a regression engine trained to correlate peak intensities and positions with drug concentration values. The result is a quantitative output indicating not only the presence of a drug but also its approximate concentration in nanograms or picograms per milliliter. This output is referenced against stored therapeutic windows to determine whether the detected level falls within a typical dosing range or suggests sub-therapeutic exposure or possible accumulation.

The end result is a comprehensive diagnostic output from the report generator 114 that displays the name of each detected drug, the estimated concentration, and an interpretive status indicating therapeutic relevance. This real-time capability supports use cases such as confirming medication adherence, assessing treatment efficacy, and detecting adverse drug accumulation in sensitive populations.

The method of use is similarly streamlined. Raman spectra are acquired non-invasively from the central anterior chamber, which functions as a representative compartment for soluble drug molecules due to continuous aqueous humor 138 flow. The AI-enhanced Raman spectroscopy diagnostic system 112 processes the spectral data, identifies drug-specific patterns, quantifies their concentrations, and generates a clinician-facing diagnostic report. This workflow enables routine, chairside pharmacologic analysis without the need for invasive sampling, laboratory-based assays, or complex interpretation procedures.

There are several approaches for SERS in aqueous humor 138 (In Vivo). The first uses a surface-coated or embedded probe (Preferred for Ophthalmic Use). A fiber-optic or contact probe may have SERS-active metallic nanostructures fixed on the tip or behind a transparent window. No nanoparticles are injected, and a Raman laser excites molecules near this surface when it's placed in contact with or close to the aqueous humor 138.

The second approach uses a microstructured implant or retractable substrates. The devices (e.g., retractable nanoarrays) may briefly enter the aqueous humor 138 space with coated SERS-active surfaces. These are removable, do not release particles, and could be integrated into a stent or diagnostic catheter.

The third approach uses free nanoparticle injection. In some animal studies, metallic nanoparticles (e.g., gold nanostars or silver colloids) are injected into the anterior chamber of the eye 102. These particles bind to target molecules, allowing strong enhancement.

Through the disclosed AI-enhanced Raman spectroscopy diagnostic system 112, clinicians gain a non-invasive tool for real-time drug detection and monitoring, making it possible to link pharmacologic treatment directly to ocular biomolecular status, thus advancing both individualized therapy and system-level treatment validation.

Non-Ocular Detection

The AI-enhanced Raman spectroscopy diagnostic system 112 include embodiments wherein spectral analysis of the aqueous humor 138 is used to identify molecular signatures associated with non-ocular medical conditions. Because the aqueous humor 138 is derived from plasma and maintains physiologic exchange with systemic circulation through the ciliary body and blood-aqueous barrier, it serves as a viable source of metabolic, inflammatory, or pharmacologic biomarkers.

In one embodiment, the AI-enhanced Raman spectroscopy diagnostic system 112 detects metabolic imbalances such as elevated glucose or lactic acid levels that may correlate with diabetes mellitus or systemic hypoperfusion. Evidence from the literature supports a measurable correlation between aqueous humor 138 and plasma glucose levels within clinically relevant ranges. In another embodiment, circulating inflammatory markers such as IL-6 or TNF-α are identified in the aqueous humor 138, allowing for the detection of systemic infections or autoimmune disorders.

The artificial intelligence engine 202 interprets these signatures in the context of pre-trained AI/ML interpretation model 134 that map Raman spectral patterns to known systemic disease states. These include psychiatric drug levels, nephrotoxins, immunosuppressants, and illicit substances. Prior studies and toxicology data have confirmed the presence of systemic drugs in aqueous humor 138 in both experimental and forensic settings. The output of the AI-enhanced Raman spectroscopy diagnostic system 112 can assist clinicians in diagnosing or monitoring non-ocular conditions through a minimally invasive ophthalmic interface.

This embodiment broadens the clinical utility of the Raman-based system beyond ocular diagnostics and supports its role in systemic disease surveillance, toxicologic screening, and personalized medicine.

The present inventions also relate to an AI-enhanced Raman spectroscopy diagnostic system 112 configured to detect and analyze non-ocular biomarkers including systemic pharmaceutical agents, illicit substances, therapeutic drug concentrations, and metabolic compounds such as glucose. The Raman spectral data is obtained non-invasively from the aqueous humor 138 in the anterior chamber of the eye 102.

interpretation models 134 may be trained on reference spectra to provide real-time concentration estimates for detected drugs. These estimates may be used to monitor therapeutic windows or detect toxicity, especially in high-risk pharmacologic agents.

Glucose

In a further embodiment, glucose-specific Raman signals are isolated and enhanced via SERS, allowing the AI-enhanced Raman spectroscopy diagnostic system 112 to estimate glucose concentrations in the aqueous humor 138. Glucose has a distinct Raman spectral signature, particularly in the regions of:

~1125 cm$^{-1}$ (C—O stretching),
~1340 cm$^{-1}$ (CH bending),
~1460 cm$^{-1}$ (CH$_2$ bending).

TABLE 18

| Non-Ocular Conditions Detectable via Aqueous Spectroscopy | | |
| --- | --- | --- |
| Condition | Detectable Marker in Aqueous Humor | Raman Detectable? |
| Diabetes Mellitus | Glucose, advanced glycation end products (AGEs) | Yes |
| Chronic Kidney Disease | Urea, creatinine | Yes |
| Drug use (e.g., opioids) | Fentanyl, morphine, cocaine metabolites | With SERS |
| Sepsis or systemic infection | Cytokines (IL-6, TNF-α) | With enhancement |
| Neurodegeneration | 8-OHdG, oxidative stress markers | Yes |
| Psychiatric treatment | SSRIs, antipsychotic agents | Yes, drug-specific |

The aqueous humor 138 serves as a biologically relevant medium for detecting systemic biomarkers due to its plasma-derived composition and optical clarity. The proposed system integrates surface-enhanced Raman spectroscopy (SERS) and AI/ML interpretation models 134 to recognize molecular vibrational patterns characteristic of clinical compounds of interest.

In one embodiment, the AI-enhanced Raman spectroscopy diagnostic system 112 detects systemically administered drugs that are not intended for ophthalmic use, such as immunosuppressants, antiepileptics, psychotropic medications, or anticoagulants. Such detection enables non-invasive drug monitoring and therapeutic compliance assessments without the need for systemic blood sampling.

In another embodiment, illicit drugs—such as fentanyl, methamphetamine, cocaine, and THC—are detected via their known vibrational signatures using SERS. A Raman spectroscopy probe 142 of fixed-position SERS Raman probe 714 interfaces with the corneal surface or limbal region without requiring internal fluid sampling or injection of free nanoparticles, ensuring biocompatibility and regulatory compliance.

The AI-enhanced Raman spectroscopy diagnostic system 112 may also include quantitative capabilities. The AI/ML Because glucose concentration in the aqueous humor 138 correlates with blood glucose, Raman analysis of aqueous humor 138 may be used as a minimally invasive proxy for blood samples. These vibrations allow glucose to be specifically identified and quantified from a complex biological matrix like blood, interstitial fluid, or aqueous humor 138. These values are interpreted by AI algorithms and correlated with systemic blood glucose levels. The AI-enhanced Raman spectroscopy diagnostic system 112 offers a non- or minimally invasive ophthalmic adjunct for diabetic management.

Therapeutic Monitoring

Lastly, the AI-enhanced Raman spectroscopy diagnostic system 112 supports real-time pharmacologic compliance detection, identifying whether patients have ingested prescribed medications. This can be of use in clinical trials, behavioral health, transplant care, and chronic disease management.

Raman spectroscopy—especially in its enhanced form (e.g., SERS)—can be used to detect and quantify a variety of drugs that require close therapeutic monitoring, particularly those with narrow therapeutic windows or high toxicity risks.

TABLE 19

| Drugs Commonly Monitored and Detectable with Raman/SERS | | | |
| --- | --- | --- | --- |
| Drug Class | Examples | Clinical Monitoring Relevance | Raman/SERS Feasibility |
| Immunosuppressants | Cyclosporine, Tacrolimus | Post-transplant therapy; requires tight control | ✓ Proven in serum with SERS |
| Antiepileptics | Carbamazepine, Phenytoin, Valproate | High toxicity at overdose; variable metabolism | ✓ Detectable with Raman |
| Anticoagulants | Warfarin, Heparin, DOACS | Overdose risk; needs INR/blood-level monitoring | ✓ Detectable via SERS |

TABLE 19-continued

| | | Drugs Commonly Monitored and Detectable with Raman/SERS | |
|---|---|---|---|
| Drug Class | Examples | Clinical Monitoring Relevance | Raman/SERS Feasibility |
| Antibiotics | Vancomycin, Gentamicin | Narrow therapeutic index; nephrotoxic | ✓ Demonstrated with SERS |
| Anti-cancer drugs | Methotrexate, Doxorubicin | High toxicity; plasma-level monitoring required | ✓ Quantified with SERS |
| Psychotropics | Lithium, Clozapine | Risk of neurotoxicity, agranulocytosis, or cardiac effects | ✓ Lithium has unique Raman peaks |
| Antiretrovirals | Efavirenz, Tenofovir | Monitored for resistance or adherence | ✓ Feasible in plasma/SERS |

Raman Is Useful for Drug Monitoring because Raman detects specific vibrational modes unique to drug molecules, permitting molecular fingerprinting. The intensity of peaks correlates with concentration, allowing a quantitative capability. The AI-enhanced Raman spectroscopy diagnostic system 112 requires minimal sample preparation, which is especially useful in plasma, serum, saliva, and potentially aqueous humor 138. SERS enhances the detection of trace drugs by amplifying weak signals by $10^6$-$10^{10}\times$ using metallic nanostructures, and enabling detection at nanomolar or lower concentrations, ideal for drugs in small-volume biofluids. SERS also allows for development of portable or point-of-care diagnostic tools.

Raman spectroscopy—particularly SERS-enhanced—is a powerful emerging tool for detecting and quantifying clinically important drugs that require close monitoring and its use with aqueous humor 138 provides many opportunities to identify drugs and metabolic levels.

The inventions thus provide a minimally invasive, AI-enhanced diagnostic platform that expands the clinical utility of ocular Raman spectroscopy into fields such as toxicology, endocrinology, pharmacokinetics, and forensic medicine.

removed from the eye 102 (perhaps placed in glassware or a slide) and analyzed with the AI-enhanced Raman spectroscopy diagnostic system 112 separately from the eye 102. The interaction between the laser 106 and intraocular tissue generates Raman-scattered light, which returns along the same optical path. A beam splitter 108 is positioned to intercept the backscattered light and redirect the Raman-scattered photons into a charge-coupled device 110 while allowing the laser to pass into the eye 102. The spectrometer 116, which receives data from the charge-coupled device 110, receives and processes the scattered light into digital spectral data. This data is then transmitted to computer 118, where spectral features are analyzed using an artificial intelligence engine 202. Diagnostic insights, including biomarker identification and classification of a diagnosis, are output through a user interface 132 for clinical interpretation. FIG. 1 also highlights the seamless flow of optical and digital signals from excitation to diagnosis, demonstrating how signal integrity and clinical feedback are preserved through each stage of the AI-enhanced Raman spectroscopy diagnostic system 112.

In some embodiments, the laser 106, the beam splitter 108, the charge-coupled device 110, and the spectrometer

TABLE 20

| | Systemic Conditions Detectable via Aqueous Humor Raman Spectroscopy | | |
|---|---|---|---|
| Systemic Condition | Representative Biomarkers in Aqueous Humor | Raman Detectable? | AI Diagnostic Application |
| Diabetes Mellitus | Glucose, AGEs (advanced glycation end products) | Yes | Non-invasive glucose estimation; diabetes screening |
| Opioid or Illicit Drug Use | Fentanyl, morphine, methamphetamine, cocaine | Yes (via SERS) | Toxicology, legal or compliance monitoring |
| Systemic Inflammation/ Sepsis | IL-6, TNF-$\alpha$, C-reactive protein | With enhancement | Early sepsis detection, systemic inflammatory state |
| Renal Failure/ Uremia | Urea, creatinine, uric acid | Yes | Monitoring nitrogenous waste products |
| Psychiatric Drug Monitoring | SSRIs, antipsychotics, benzodiazepines | Yes | Medication adherence and therapeutic level checks |
| Endocrine Disorders | Cortisol, insulin (via metabolites or precursors) | Emerging | Adrenal stress and metabolic profiling |
| Neurodegeneration | 8-OHdG, lipid peroxidation products | Yes | Oxidative stress profiling |

FIG. 1 depicts a representative system architecture of the AI-enhanced Raman spectroscopy diagnostic system 112. In this figure, a laser 106, such as a monochromatic excitation laser, is directed into the eye 102 through the cornea and lens, focusing light onto the posterior segment, specifically targeting the aqueous humor 138 or an intraocular anomaly 104. In some embodiments, the aqueous humor 138 may be 116 may be integrated into a handheld Raman spectroscopy probe 142. The Raman spectroscopy probe 142 may be mounted on a standard ophthalmic slit lamp adapter, which stabilizes both the Raman spectroscopy probe 142 and the patient's eye during examination. The probe optics include the laser 106 with a focusing lens assembly and an optical filter 140 for rejecting Rayleigh scattered light while capturing inelastic Raman scatter.

In the process shown in FIG. 1, the laser 106 is directed into the eye 102 through a shared optical system that includes video transmission capability. Raman-scattered light reflected from the aqueous humor 138 returns along the same optical path. The returning light is diverted by a beam splitter 108 toward a charge-coupled device 110, which converts the scattered light into raw spectral data. A Raman spectrometer 116 uses diffraction gratings to disperse the light and measure Raman shifts corresponding to molecular vibrations. The spectrometer 116 sends spectral data in digital format to the computer 118, where the one or more processors 124 use the artificial intelligence engine 202, which analyzes the spectral signature to detect molecular features indicative of melanin, protein, or lipid content— biomarkers associated with intraocular anomalies 104. The artificial intelligence engine 202 interprets the data and transmits the diagnostic output (including classification results, molecular probabilities, and other indicators) to a user interface 132 for clinical review.

The computer 118 may have one or more processors 124 communicatively connected to one or more network interfaces 126 and one or more storage 122 devices. The storage 122 may include memory 120, such as random access memory, read-only memory, and similar. Storage 122 may also include longer-term storage 220 devices such as optical storage, disk drives, solid state drives, and similar. The storage 122 may include non-transitory instructions for the processors 124, one or more spectral data acquisition modules 208, and one or more artificial intelligence engines 202. The computer 118 may be communicatively connected to one or more user interfaces 132, such as a computer monitor, a keyboard, a touchscreen, a mouse, a laptop, a tablet, a smartphone, a smart watch, another computer, or a similar device. The connection between the computer 118 and the user interface 132 may be through the network interface 126 to a network or the connection may be through wires or wireless. The network interface 126 may be operatively coupled to the Internet and/or to a cloud-based computing environment.

Note that some (or all) of the functionality shown here in the computer 118 could be incorporated in the spectrometer 116. In some embodiments, the Optical Coherence Tomography 136 functionality could also be integrated with the spectrometer 116 and/or the computer 118.

In one embodiment, the Raman excitation beam from the laser 106 is projected along the central optical axis of the eye 102 and focused within the central region of the anterior chamber. This configuration enables consistent, non-contact alignment and facilitates integration with clinical examination platforms such as slit lamps or handheld probes. The aqueous humor 138 acts as a dynamic, well-mixed medium, allowing centrally focused Raman acquisition to capture dispersed biomarkers originating from peripheral ocular structures, including the trabecular meshwork, Schlemm's canal, iris, and ciliary body.

The system's artificial intelligence component is trained on centrally acquired spectral datasets to identify and classify disease-relevant molecular patterns, even at diluted concentrations. This central acquisition strategy reduces anatomical variability, enhances reproducibility, and enables rapid, patient-friendly diagnostic screening of soluble biomarkers associated with intraocular pressure, oxidative stress, inflammation, and metabolic dysfunction. Considerations for sampling are listed in Table 5: Target Sampling Caveats and Limitations.

In certain embodiments, the disclosed AI-enhanced Raman spectroscopy diagnostic system 112 enhances diagnostic reliability by employing temporal averaging, time-aware normalization, and anatomical inference based on spectral features. During a single scan session, multiple Raman spectra may be acquired and averaged to minimize stochastic noise and improve signal fidelity. This approach increases the robustness of spectral classification, particularly in the presence of ambient lighting variability or minor ocular motion.

To address potential variability due to diurnal biomarker fluctuation, the AI-enhanced Raman spectroscopy diagnostic system 112 includes time-of-day normalization strategies based on known circadian expression patterns of aqueous biomarkers. This normalization allows for consistent interpretation of measurements collected at different times.

Additionally, the AI/ML interpretation model 134 is trained to infer the approximate anatomical origin of a given spectrum-central vs. peripheral-based on signal shape, intensity, and feature distribution, even in the absence of explicit Raman spectroscopy probe 142 position metadata. This inferred location informs a context-adjusted confidence score, further supporting accurate, explainable diagnostic decision-making.

System Architecture

The AI-enhanced Raman spectroscopy diagnostic system 112 may comprise a compact handheld Raman spectroscopy probe 142, capable of capturing high-resolution spectra from intraocular biomolecules by directing near-infrared excitation light through the clear cornea into the 138. For clinical stability, especially in settings requiring high reproducibility, the Raman spectroscopy probe 142 may be mounted on a standard ophthalmic slit lamp adapter, which stabilizes both the Raman spectroscopy probe 142 and the patient's eye during examination. The Raman spectroscopy probe 142 optics may include a laser 106 with a focusing lens assembly and an optical filter 140 for rejecting Rayleigh scattered light while capturing inelastic Raman scatter.

Once the Raman signal is collected by a charge-coupled device 110, it may be transmitted through a fiber optic bundle to a spectrometer 116, which digitizes the signal for AI processing. The spectral range of interest typically spans from $400 \text{ cm}^{-1}$ to $1800 \text{ cm}^{-1}$, encompassing the biochemical fingerprint region where proteins, lipids, and nucleic acids exhibit characteristic vibrational modes.

At the software layer, the inventions may deploy a tiered artificial intelligence architecture. The raw spectral data may first pass through a denoising pipeline in the spectral data acquisition module 208, which may consist of a stacked autoencoder trained on reference spectra to distinguish meaningful molecular patterns from noise or background fluorescence. This step helps to isolate weak Raman signals from biomarkers such as 8-hydroxy-2'-deoxyguanosine (8-OHdG) or TGF-β2, which may exist in picomolar concentrations in aqueous humor 138.

Following signal cleanup, the processed spectra are analyzed by a convolutional neural network (CNN classifier 128) trained to identify disease-associated spectral patterns. For example, the presence of elevated peaks near $1450 \text{ cm}^{-1}$ and $734 \text{ cm}^{-1}$ may be classified as indicative of oxidative stress consistent with glaucomatous progression. In parallel, peak shifts and intensities associated with ECM proteins such as fibronectin and laminin may suggest early trabecular meshwork remodeling. These biomarkers are used not in isolation, but as part of an AI-generated feature vector, which captures the biochemical context of the sample.

The outputs from the CNN classifier 128 may then be routed to a decision engine that performs multiple tasks: (1) classification of the spectral profile into categories such as normal, early glaucoma, advanced glaucoma, or inflammatory eye disease using the AI/ML interpretation model 134; (2) estimation of individual biomarker concentrations using regression models (e.g., support vector regression, ridge regression) in the concentration estimation module 206; and (3) integration with prior patient data, such as IOP readings and OCT scans, for temporal analysis and trend detection in the report generator 114.

The artificial intelligence engine 202 can also provide a confidence score for diagnostic output that assists in clinical decision-making. (Table 21: AI Models that Provide Confidence Estimates). In one embodiment, the artificial intelligence system utilized for Raman-based glaucoma detection incorporates a mechanism for generating confidence-weighted diagnostic outputs. This functionality is useful for clinical settings, where physicians must be able to assess not only the categorical diagnosis but also the statistical certainty with which it is rendered.

coma," "no glaucoma," or "at risk") and a quantified confidence score (e.g., "91% probability±4%"). This output is integrated into the clinician-facing interface, allowing the ophthalmologist to evaluate both the AI's recommendation and the strength of its underlying certainty. In low-confidence scenarios, the interface may recommend retesting, human override, or additional imaging.

To further enhance reliability, an ensemble of models may also be employed. The final diagnostic decision is derived from the consensus or weighted average of predictions made by multiple independently trained models. This ensemble approach reduces overfitting and increases robustness, especially in borderline cases or heterogeneous spectral profiles.

Workflow and User Interface

The Raman spectroscopy diagnostic workflow described herein is optimized for rapid, real-time application during routine clinical assessments. The procedure is modeled after well-established ophthalmic practices such as applanation tonometry and confocal microscopy, both of which involve contact with the corneal surface under topical anesthesia. The brief duration and low mechanical force involved in

TABLE 21

| AI Models that Provide Confidence Estimates |
| --- |
| 1. Probabilistic Neural Networks (PNN)/Softmax Classifiers<br>How it works: Most deep learning models (e.g., CNNs) end with a softmax layer, which outputs probabilities for each class (e.g., healthy vs. glaucoma).<br>Confidence score: The highest probability is used as the model's confidence in its prediction.<br>Use case: Good for quick classification and scalable to multi-class tasks (e.g., stratifying risk into low/moderate/high).<br>2. Bayesian Neural Networks (BNN)<br>How it works: These models treat weights as probability distributions rather than fixed values, capturing uncertainty in predictions.<br>Confidence score: They naturally output both a prediction and a confidence interval (e.g., "glaucoma: 82% ± 5%").<br>Use case: Excellent when interpretability and uncertainty are critical-ideal for medical diagnostics.<br>3. Monte Carlo Dropout (MC Dropout)<br>How it works: A technique applied to standard deep learning models like CNNs. At test time, dropout is enabled and the model is run multiple times to generate a distribution of outputs.<br>Confidence score: The variance across predictions reflects uncertainty; the average gives the prediction, and the spread gives confidence.<br>Use case: Simple to implement, widely used in medical imaging.<br>4. Ensemble Models<br>How it works: Multiple independent models (e.g., several CNNs trained with different initializations) are combined.<br>Confidence score: If all models agree, confidence is high; if they disagree, the system reports uncertainty.<br>Use case: Robust predictions, easy to apply to already trained models. |

The core AI/ML interpretation model 134 is based on a convolutional neural network (CNN), optionally combined with recurrent layers for longitudinal data integration. To estimate diagnostic confidence, the system employs Monte Carlo Dropout (MC Dropout) during inference. This technique enables the neural network to simulate Bayesian behavior by stochastically dropping units in the network at test time, resulting in multiple forward passes over the same input data. The variance among these outputs is used to compute a confidence interval around the final classification.

Alternatively, a Bayesian Neural Network (BNN) may be employed to directly model uncertainty. Unlike conventional deterministic networks, a BNN assigns probability distributions to its weights, enabling it to quantify epistemic uncertainty—uncertainty due to limited training data—and aleatoric uncertainty, which is inherent in the spectral measurements themselves.

The AI-enhanced Raman spectroscopy diagnostic system 112 may output both a classification result (e.g., "glau- Raman acquisition make this protocol well-tolerated in both screening and diagnostic settings.

For each eye 102, the process begins with Raman spectroscopy probe 142 alignment and patient preparation, which typically takes about ten seconds. One or two drops of a standard ophthalmic anesthetic solution such as proparacaine hydrochloride 0.5% are instilled into the conjunctival sac of the eye to be tested. The anesthetic is allowed to take effect over 60-90 seconds. During this time, the hand-held or slit lamp-mounted Raman spectroscopy probe 142 is positioned along the central optical axis of the eye 102, ensuring stable focus on the anterior chamber. Once aligned, Raman excitation is initiated, and spectral data are acquired in approximately five seconds using a low-power laser 106 operating within ANSI-defined ocular safety limits.

TABLE 22

| Workflow Timing from Scan Acquisition to Results Display | | |
|---|---|---|
| Workflow Steps | Estimated Time (seconds) | Cumulative Time (seconds) |
| 1. Probe alignment and patient preparation | 10 | 10 |
| 2. Raman excitation and spectral acquisition | 5 | 15 |
| 3. Signal preprocessing (denoising, baseline correction, normalization) | 3 | 18 |
| 4. Spectral analysis and biomarker classification by AI | 2 | 20 |
| 5. Concentration estimation and confidence scoring | 2 | 22 |
| 6. Display of results on user interface | 1 | 23 |

Immediately following acquisition, the raw spectral data may be processed through a real-time signal preprocessing pipeline in the spectral data acquisition module 208. This may include baseline correction, noise filtering, and normalization, all of which are completed within three seconds. The cleaned spectral data may then be analyzed by an AI/ML interpretation model 134 trained to detect and classify disease-relevant biomarkers. This spectral analysis and classification phase takes roughly two seconds. Following classification, a concentration estimation module 206 may calculate the relative abundance of identified biomarkers and generates a confidence score reflecting the integrity and reliability of the scan. These final analytic steps may require an additional two seconds. Finally, the diagnostic output, including biomarker identity, estimated concentration and interpretive flags, may be rendered by the report generator 114 on the user interface 132 in less than one second.

In total, the full workflow from scan acquisition to result display for a single eye 102 may be completed in approximately 23 seconds, enabling efficient, and chairside diagnostics. For both eyes 102, the procedure can be completed within 40 to 45 seconds, assuming immediate repositioning and consecutive scanning. See Table 22: Workflow Timing from Scan Acquisition to Results Display. In bilateral cases, while scanning time effectively doubles, several computational steps such as preprocessing and inferencing may be parallelized or optimized to reduce total session time. This highly streamlined process supports near-instantaneous diagnostic interpretation, making it well-suited for high-throughput clinical settings and longitudinal patient monitoring.

The user interface 132 of the AI-enhanced Raman spectroscopy diagnostic system 112 may display both the spectral readout and the diagnostic interpretation, including a disease probability score, biomarker concentration table, and a graphical history of changes across multiple visits. Clinicians can review individual spectral features and compare them to normative ranges, enabling personalized treatment planning.

Figure 2:
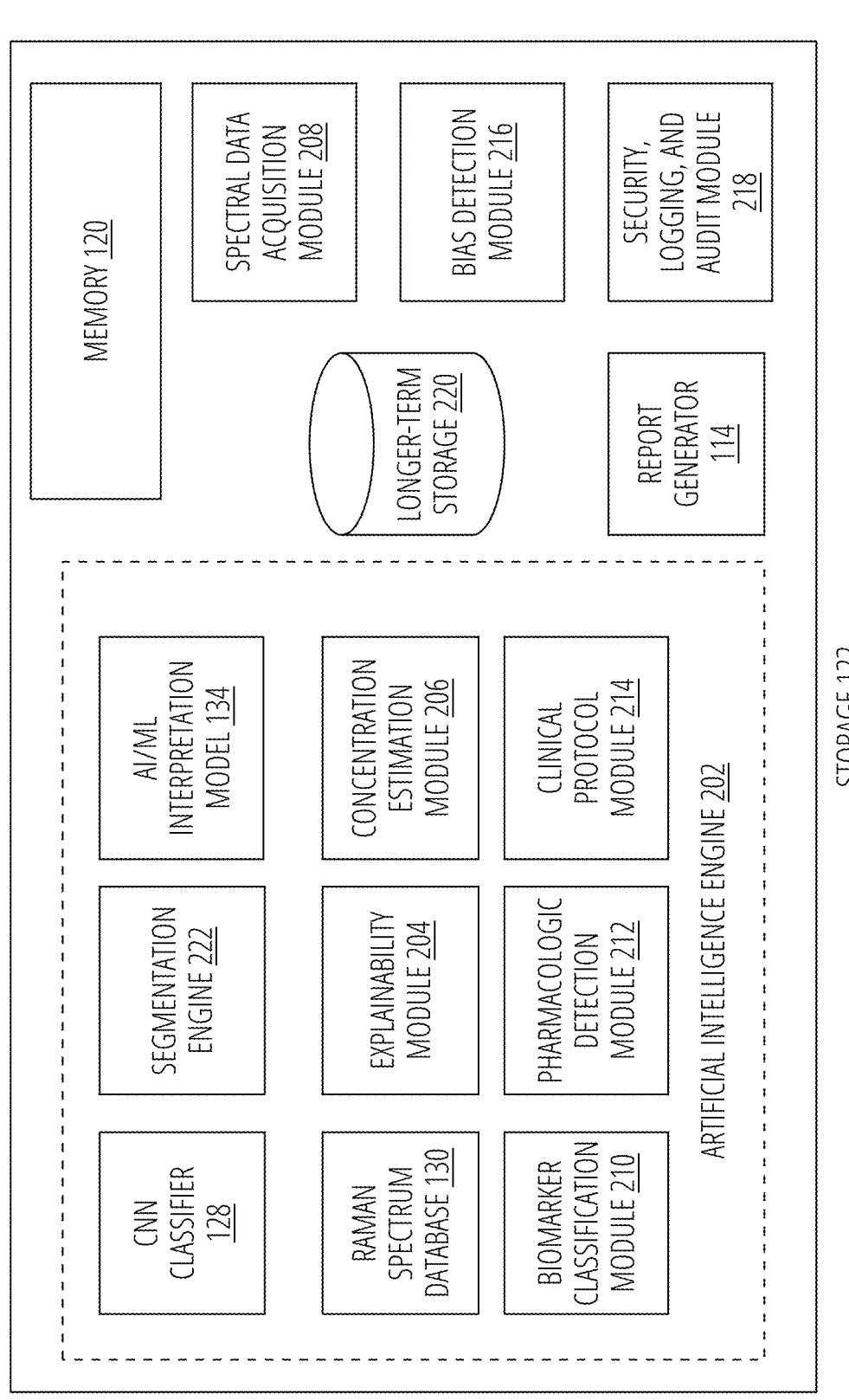
FIG. 2 details the storage aspect of the system architecture of the AI-assisted Raman diagnostic system.

FIG. 2 shows the storage 122 in more detail. What is shown is one or many possible embodiments. Storage 122 may include physical memory 120 and longer-term storage 220 devices. Either the memory 120 or longer-term storage 220 may include non-transitory instructions for the processors 124, either as direct instructions, interpretative instructions, artificial intelligence engines, or artificial intelligence models.

The storage 122 may include a spectral data acquisition module 208 for receiving data from the spectrometer 116 and/or the charge-coupled device 110 and processing this data into a format usable by the artificial intelligence engine 202. The spectral data acquisition module 208 may also receive data from an Optical Coherence Tomography 136 device. The spectral data acquisition module 208 may also collect information on the time the data is received.

The storage 122 could also incorporate a bias detection module 216 to monitor the artificial intelligence engine 202 for data shifts and bias. Should bias be detected, one or more of the models in the 202 may be retrained.

The storage 122 may also include a security, logging, and audit module 218 to maintain compliance with privacy laws and clinical data standards (e.g., GDPR, HIPAA, FDA guidance).

The storage 122 may also include one or more artificial intelligence engines 202 to process the spectral data from the spectral data acquisition module 208 into information useful for clinical diagnosis. The artificial intelligence engine 202 may have a Raman spectrum database 130 (or a plurality of Raman spectrum databases 130) that provides the data from converting the spectral data from the spectral data acquisition module 208 into biomarkers to be used by the AI/ML interpretation model 134.

The artificial intelligence engine 202 may (or may not) have a number of software modules such as one or more CNN classifiers 128, one or more AI/ML interpretation models 134, one or more explainability modules 204, one or more concentration estimation modules 206, one or more biomarker classification modules 210, one or more pharmacologic detection modules 212 and/or one or more clinical protocol modules 214.

The CNN classifier 128 may be based on a convolutional neural network (CNN) or hybrid AI model and is trained on spectra from normal aqueous humor 138 and aqueous humor 138 with ocular diseases. It compares each scan against a reference database to estimate the presence and severity of the anomalies.

The report generator 114 may collect and organize the results of the AI/ML interpretation model 1344, the explainability module 204, the concentration estimation module 206, the biomarker classification module 210, the pharmacologic detection module 212, and/or the clinical protocol module 214 into a report for a physician or patient. The report may be sent to the user interface 132.

An Artificial Intelligence/Machine Learning interpretation model 134 ("AI/ML interpretation model 134") may analyze the spectral data to identify molecular patterns associated with ocular diseases or intraocular anomalies 104. The AI/ML interpretation model 134 may incorporate deep learning algorithms and support adaptive and federated learning models, allowing it to dynamically incorporate newly discovered biomarkers post-deployment.

To support clinical adoption, the artificial intelligence engine 202 may include an explainability module 204, such as Grad-CAM and SHAP, which highlight the precise Raman spectral regions that influenced the model's decision. The explainability module 204 allows clinicians to verify whether a prediction is driven by peak intensity, shape, or molecular degradation pattern.

A concentration estimation module 206 may calculate the relative abundance of identified biomarkers and generate a confidence score reflecting the integrity and reliability of the scan.

The biomarker classification module 210 may be based on a convolutional neural network (CNN) or hybrid AI model and is trained on spectra from normal aqueous humor 138 and aqueous humor 138 with ocular diseases. It compares each scan against a database of biomarkers to estimate the presence and severity of ocular diseases.

The pharmacologic detection module 212 is designed to analyze the presence of drugs within the aqueous humor 138. This capability enhances diagnostic value by enabling the AI-enhanced Raman spectroscopy diagnostic system 112 not only to detect disease biomarkers, but also to evaluate the ocular pharmacokinetics of therapeutically applied agents.

The clinical protocol module 214 uses the identified biomarkers and the ocular pharmacokinetics to identify treatment options.

Segmentation Engine and Anatomical Targeting

In certain embodiments, the artificial intelligence engine 202 includes a segmentation engine 222 configured to identify and delineate anatomical regions within structural imaging datasets, including Optical Coherence Tomography 136 (OCT), anterior segment ultrasound, or Raman-responsive spatial maps of the anterior chamber. Segmentation refers to the computational process by which the AI-enhanced Raman spectroscopy diagnostic system 112 assigns anatomical labels to each pixel or voxel of imaging data, thereby enabling tissue-specific targeting of Raman excitation and interpretation.

The segmentation engine 222 allows the AI-enhanced Raman spectroscopy diagnostic system 112 to distinguish between closely situated or overlapping structures, such as Schlemm's canal, the trabecular meshwork (TM), the iris root, corneal endothelium, and the aqueous interface. Accurate delineation is critical in the anterior segment, where these structures occupy adjacent anatomical planes and exhibit distinct biochemical profiles.

The output of the segmentation engine 222 may be used to direct Raman excitation or signal collection to specific anatomical zones of interest (e.g., the inner wall of Schlemm's canal or trabecular meshwork band). The output may exclude signals originating from confounding regions such as the peripheral iris or corneal stroma. The output may dynamically adjust probe angle, depth, or confocal plane in mounted or handheld use. The output may enable localized calibration of AI spectral classifiers based on region-specific Raman signatures. And the output may mask biologically inactive or optically noisy zones from downstream interpretation.

To implement this functionality, the segmentation engine 222 may employ one or more supervised machine learning architectures. For instance, convolutional neural networks (CNNs) may be trained to identify the scleral spur and posterior corneal curvature in cross-sectional OCT for trabecular meshwork boundary localization. 3D U-Net architectures may be applied to volumetric image stacks to map Schlemm's canal across spatial planes. Transformer-based models may be used to integrate context across wide anterior fields, accounting for anatomical variability across individuals and age groups.

Segmentation improves the effective diagnostic signal quality by increasing the signal-to-noise ratio, eliminating non-relevant spectral contributions, and enhancing biomarker specificity. This is particularly critical for Raman-based detection of early glaucoma biomarkers (e.g., nitric oxide synthase, prostaglandin metabolites, or oxidative stress markers), which may be spatially confined to the trabecular meshwork or Schlemm's canal interface and otherwise lost in blended spectra.

Clinically, segmentation supports more accurate identification and quantification of region-specific biomarkers and the differentiation of early-stage pathologic changes from global aqueous alterations. The segmentation supports the longitudinal tracking of biochemical changes in defined anatomical compartments and the reduction in false negatives or variability caused by probe misalignment or broad sampling. Segmentation minimizes unnecessary invasive diagnostics through targeted, reproducible measurements.

Segmentation thus plays a foundational role in aligning anatomical structure with biochemical interpretation, making the AI-enhanced Raman spectroscopy diagnostic system 112 suitable for early detection, treatment monitoring, and comparative analysis of localized disease progression in glaucoma, uveitis, or other anterior segment disorders.

The diagnostic advantages of segmentation in aqueous humor 138 analysis are multifactorial. First, segmentation improves the specificity of Raman-based biomarker detection by ensuring that spectral data is acquired from anatomically relevant tissues such as the trabecular meshwork or Schlemm's canal, thereby reducing false positives due to blended or misaligned signals. Second, by allowing the artificial intelligence engine 202 to interpret molecular signatures in anatomically segmented zones, the AI-enhanced Raman spectroscopy diagnostic system 112 can distinguish between biomarker patterns arising from normal, early-pathologic, or disease-specific tissue states. Third, segmentation enables quantitative tracking of biomarker changes over time in fixed regions of interest, supporting non-invasive, longitudinal monitoring of disease progression or treatment efficacy, particularly in glaucoma and anterior uveitis. Finally, segmentation-guided Raman acquisition improves reproducibility and may reduce the need for more invasive or intraocular sampling procedures in diagnostic workflows. These advantages collectively enhance the diagnostic accuracy, safety, and clinical value of the AI-enhanced Raman spectroscopy diagnostic system 112 in anterior segment biomarker analysis.

TABLE 23

| Segmentation Improvement of Effective Signal Quality | |
| --- | --- |
| Benefit | Description |
| Noise Reduction | Segmentation restricts analysis to a defined anatomical region (e.g., Schlemm's canal), excluding signals from surrounding irrelevant tissues (iris, sclera, etc.). |

TABLE 23-continued

Segmentation Improvement of Effective Signal Quality

| Benefit | Description |
| --- | --- |
| Improved Signal-to-Noise Ratio (SNR) | By filtering out non-target regions, the proportion of meaningful spectral data increases. |
| Anatomical Precision | Ensures that Raman data is matched to the correct biological structure (e.g., TM vs cornea). |
| Targeted Calibration | Enables use of tissue-specific AI models, improving biomarker recognition accuracy. |
| Laser/Optical Alignment | Informs probe positioning, which indirectly improves signal consistency and focus. |
| Avoidance of Artifacts | Helps eliminate spectral contamination from pigmented or optically dense structures. |

Surrogate Biomarkers and Therapeutic Detection

In certain embodiments, the disclosed AI-enhanced Raman spectroscopy diagnostic system 112 is configured not only to detect disease-associated biomarkers, but also to identify and quantify pharmaceutical agents present within the anterior chamber of the eye 102 as surrogate biomarkers. As used herein, a "surrogate biomarker" refers to a pharmacologic substance whose presence, absence, or concentration provides inferential insight into disease activity, therapeutic response, or patient adherence, even if the substance itself is not inherently pathological.

Pharmaceutical agents, whether delivered topically, orally, intravenously, or via intraocular implants, may persist in the aqueous humor 138 in concentrations sufficient to generate identifiable Raman spectral features. These agents include, but are not limited to: Prostaglandin analogs (e.g., latanoprost, bimatoprost), beta-blockers (e.g., timolol), carbonic anhydrase inhibitors (e.g., dorzolamide), alpha-2 adrenergic agonists (e.g., brimonidine), corticosteroids (e.g., prednisolone acetate), immunomodulatory agents, antimetabolites, and investigational biologics.

The AI/ML interpretation model 134 embedded within the AI-enhanced Raman spectroscopy diagnostic system 112 is trained to detect spectral features associated with these compounds and estimate their concentrations using regression models. Upon detection, the AI-enhanced Raman spectroscopy diagnostic system 112 interprets the presence or relative abundance of these compounds as clinical correlates: detection of latanoprost or brimonidine may imply a current or historical diagnosis of glaucoma or ocular hypertension, elevated levels of corticosteroids may indicate active treatment for uveitis, post-surgical inflammation, or immune-mediated conditions, absence of expected pharmacologic signatures, especially when prior treatment is documented, may raise flags for non-adherence or dosing errors.

These pharmaceutical agents act as contextual biomarkers, enabling the AI-enhanced Raman spectroscopy diagnostic system 112 to refine diagnostic interpretations based on therapeutic exposure. The presence or absence of a drug signature can influence how the AI-enhanced Raman spectroscopy diagnostic system 112 classifies disease activity, adjusts confidence metrics, and informs treatment decision support. For example, if a biomarker signature suggests inflammation but corticosteroids are detected within the therapeutic range, the AI output may classify the condition as controlled disease rather than an active flare. The diagnostic output can include the drug name, an estimated concentration, and an assessment of whether the level falls within, above, or below the expected therapeutic range.

The detection method for pharmaceuticals in aqueous humor 138 using Raman spectroscopy can involve spectral acquisition with a 785 nm wavelength laser 106, within a detection range of 400 to 1800 cm 1, AI trained to recognize drug-specific Raman peaks, regression models to estimate drug concentration.

This detection capability enables real-time pharmacokinetic assessments, facilitating evaluation of drug absorption, metabolic clearance, and therapeutic efficacy directly within the anterior chamber. In this sense, the pharmaceutical agents become dynamic surrogate indicators of clinical state and therapeutic adequacy.

By treating pharmacologic agents as surrogate biomarkers, the AI-enhanced Raman spectroscopy diagnostic system 112 enhances its diagnostic specificity and utility, bridging molecular analysis with real-world treatment context in a non-invasive, real-time platform.

Biomarker Transformation

Biomarkers may be released into the aqueous humor 138 through several biological mechanisms, many of which are influenced by local physiological or pathological conditions. Of particular interest are the endothelial cells lining Schlemm's canal—a key drainage structure located at the iridocorneal angle—which contribute molecular content through three primary pathways: shedding of membrane-bound components, active secretion of signaling molecules, and the release of intracellular contents following exposure to mechanical shear stress or injury.

A representative example is interleukin-6 (IL-6), a pro-inflammatory cytokine secreted by Schlemm's canal endothelial cells. At its point of release near the angle of the anterior chamber, IL-6 may exist in relatively high concentrations and in a bioactive form. However, as it diffuses through the aqueous humor 138 toward the central anterior chamber, IL-6 is subject to several transformations—including dilution, enzymatic degradation, and binding to soluble receptor proteins—that can alter its structural integrity, concentration, and bioactivity.

Other biomarkers undergo similar biochemical modifications during transit. For instance, intercellular adhesion molecule-1 (ICAM-1) can be cleaved into a soluble fragment that retains partial diagnostic utility, but may exhibit shifted or diminished spectral features. Vascular endothelial growth factor (VEGF), another relevant biomolecule, can become bound to soluble VEGF receptors (VEGF-R), masking its free, active form from direct detection. In inflammatory microenvironments enriched in reactive oxygen species (ROS), oxidative modifications may further alter biomarkers, resulting in peak shifts or broadened Raman signals. In addition, many biomarkers are not free-floating, but are instead encapsulated within extracellular vesicles such as exosomes or microvesicles. This compartmentalization not only affects molecular transport but also presents challenges to detection, as vesicle-associated biomarkers may require additional signal processing or release mechanisms to be accurately quantified.

These complex transformation pathways underscore the importance of accounting for spatial, structural, and biochemical variability in any diagnostic system relying on in vivo biomarker profiling, especially those based on Raman spectroscopy, where spectral fidelity is useful for accurate identification.

Role of the AI-Assisted Raman Spectroscopy System in Addressing Biomarker Transformation in Aqueous Humor The aqueous humor 138 presents a molecular environment where biomarkers may undergo a range of dynamic transformations, such as degradation, cleavage, oxidation, binding, or vesicle encapsulation—before reaching the site of detection. These changes can significantly affect the intensity, location, and clarity of Raman spectral peaks, thereby complicating direct interpretation. The integration of Artificial Intelligence (AI) within the AI-enhanced Raman spectroscopy diagnostic system 112 is useful to overcoming these challenges and enabling accurate, real-time analysis.

1. Pattern Recognition of Transformed Biomarkers. The artificial intelligence engine 202, particularly when built with convolutional neural networks (CNNs), may be trained not only to recognize idealized spectral features of intact biomarkers, but also to detect the spectral signatures of modified or fragmented forms. For instance, cleaved ICAM-1 or oxidized glutathione may generate altered Raman peaks that still follow consistent transformation patterns. Through exposure to labeled training data containing these spectral variants, the AI/ML interpretation model 134 can learn to identify transformation-specific spectral shifts and intensities, thereby extending the diagnostic reach beyond intact molecules.

2. Inference of Biochemical State. AI algorithms using the AI/ML interpretation models 134 can infer the biochemical state of a biomarker based on subtle deviations from canonical spectral patterns. For example, a spectral peak that is slightly shifted or broadened may indicate oxidation, while a diminished peak intensity might reflect proteolytic degradation. By mapping these deviations to known transformation pathways, the artificial intelligence engine 202 can output an adjusted concentration estimate or classify the biomarker as "native," "bound," "oxidized," or "degraded," depending on the spectral evidence.

3. Vesicle-Associated Biomarker Detection. Extracellular vesicles may encapsulate biomarkers, shielding them from direct detection. The AI/ML interpretation model 134 can be trained to detect composite spectral profiles—characterized by overlapping features from lipids, proteins, and membrane-bound structures—that suggest the presence of vesicle-encapsulated biomarkers. In such cases, the AI-enhanced Raman spectroscopy diagnostic system 112 may flag the signal as "vesicle-associated," allowing clinicians to interpret results in light of expected encapsulation and possibly prompting complementary biochemical analysis.

4. Contextual Adjustment Using Sampling Location. Because biomarker state can vary by sampling location (e.g., central anterior chamber vs. iridocorneal angle), the AI/ML interpretation model 134 may use either explicit metadata or spectral inference to identify where in the chamber the signal was acquired. The artificial intelligence engine 202 may perform contextual inference by integrating spectral features with metadata such as sampling location, pharmacologic exposure, or patient history to refine diagnostic interpretation in real time. If degradation is more likely centrally, the AI/ML interpretation model 134 can adjust its interpretive thresholds accordingly, assigning a lower weight to biomarkers known to degrade or bind during transit. This localization-aware reasoning improves sensitivity and specificity by integrating anatomical context into molecular analysis.

5. Temporal and Physiological Context Awareness. The AI-enhanced Raman spectroscopy diagnostic system 112 also adjusts for physiological influences such as diurnal variation and therapeutic pharmacologic presence. For biomarkers like IL-6 or VEGF, whose expression and degradation may fluctuate with time of day or be modulated by medication, the AI/ML interpretation model 134 may apply normalization protocols and context-aware inference to distinguish between pathological elevation and normal circadian variation.

6. Explainability and Visualization. For clinical confidence, the artificial intelligence engine 202 may include one or more explainability modules 204 (e.g., Grad-CAM or SHAP) that highlight the specific regions of the Raman spectrum responsible for each diagnostic inference. In the case of transformed biomarkers, this may allow clinicians to see which peaks suggest oxidation, fragmentation, or complex formation, adding interpretive transparency to the automated analysis.

By integrating machine learning, spectral pattern recognition, and contextual reasoning, the AI-enhanced Raman spectroscopy diagnostic system 112 may compensate for the complexity of in vivo biomarker transformation. This may enable the system to provide reliable diagnostic output even in the face of biochemical variability, anatomical gradients, or molecular masking—making it a powerful tool for real-time, non-invasive ophthalmic diagnostics.

Incorporation of Newly Discovered Biomarkers

To support continued advancement and diagnostic versatility, the disclosed AI-enhanced Raman spectroscopy diagnostic system 112 described herein may be designed to incorporate both existing and newly discovered biomarkers. In clinical research and ophthalmology, biomarker discovery involves analyzing biofluids such as aqueous humor 138 using high-sensitivity spectroscopic or molecular techniques. Candidate biomarkers may include peptides, cytokines, metabolites, exosomes, or oxidative stress byproducts that show a statistically significant correlation with disease states such as glaucoma, uveitis, or ocular hypertension.

When new biomarkers are discovered through clinical studies, biochemical assays, or literature reports, their molecular signatures—including Raman-active vibrational bands—can be characterized and stored in the system's Raman spectrum database 130. The AI/ML interpretation model 134 used within the AI-enhanced Raman spectroscopy diagnostic system 112 may be built with modular training pipelines that allow for supervised fine-tuning on new datasets containing validated spectra from these novel biomarkers. Spectral training data for each biomarker may be augmented through computational techniques such as Gaussian noise injection, synthetic blending, and spectral interpolation to ensure robust pattern recognition.

Upon validation, newly incorporated biomarkers may be included in the biomarker classification module 210 as part of an expanded feature vector, enhancing its ability to diagnose early-stage or atypical disease presentations. A regression sub-model may also be trained to estimate concentration ranges for the newly added biomarker using standard peak intensity mappings and region-specific normalization factors.

These updates may be performed locally on clinical workstations or through federated learning across multiple clinical sites, allowing the AI/ML interpretation model 134 to evolve while preserving patient privacy. In all cases, the AI-enhanced Raman spectroscopy diagnostic system 112 ensures traceability and auditability of model changes through version tracking and validation reporting. As a result, the platform remains capable of adapting to and incorporating subtle, novel biomarkers that reflect emergent understanding of ocular disease.

TABLE 24

| Integration of Newly Discovered Biomarkers |
|---|

1. Biomarker Discovery
→ Identification of novel biomarkers through clinical studies, spectroscopic screening, or molecular assays.
→ Candidate biomarkers include cytokines, metabolites, miRNAs, exosomes, and stress-response proteins.
2. Molecular Characterization
→ Spectral analysis to define Raman-active vibrational bands.
→ Verification of diagnostic relevance through correlation with disease states (e.g., glaucoma).
→ Baseline establishment of concentration ranges and expression patterns.
3. Incorporation into System Database
→ Entry of spectral fingerprint into internal reference library.
→ Classification of biomarker by disease association and molecular category.
→ Flag for supervised AI training update.
4. AI Model Retraining and Integration
→ Fine-tuning of neural networks and regression models using new labeled data.
→ Data augmentation applied (noise injection, interpolation, synthetic spectra).
→ Federated learning may be used for privacy-preserving model update across clinics.
5. Diagnostic Deployment and Explainability
→ New biomarker incorporated into real-time classification and quantification workflows.
→ Grad-CAM or SHAP visualizations display spectral regions contributing to predictions.
→ System logs model version and update path for regulatory traceability.

The inclusion of an explainability module 204, such as Grad-CAM or SHAP, further supports this process by allowing researchers and clinicians to visualize how newly detected spectral features contribute to diagnostic predictions. This transparency ensures that emerging biomarkers can be rapidly evaluated for clinical relevance and integrated into the AI-enhanced Raman spectroscopy diagnostic system 112 without compromising diagnostic consistency or interpretability.

Context-Aware AI Framework

Table 25 Context-Aware Artificial Intelligence: Framework for Raman Spectroscopy shows commonly observed context-aware variables that may require AI adjustment, and Table 26 Systemic Integration Strategies for these Variables provides system integration strategies for these variables. The strategic flow of adjustment, validation, and confidence scoring for the inventions that address the variables is shown in Table 27 AI Flow Description: Context-Awareness Spectral Analysis Pipeline.

TABLE 25

| Context-Aware Artificial Intelligence: Framework for Raman Spectroscopy | | |
|---|---|---|
| Variable | Effect | AI Adjustment Strategy |
| Age | Shifts in cytokine, oxidative, and structural biomarker baselines | Include age as input feature; age-stratified models |
| Sex | Hormonal differences impact biomarker expression | Sex-aware thresholds or bias checks |
| Systemic diseases | Affects immune and metabolic markers | Diagnosis flags as input; model calibration |
| Ocular surgery/trauma | Elevated inflammatory markers | Flag cases; modify interpretation window |
| Contact lens wear | May affect tear film diffusion or oxygenation | Exclude or adjust confidence weighting |
| Hydration/metabolism | Affects metabolic and osmotic balance | Include hydration status if available |
| Post-treatment timing | Alters biomarker pharmacokinetics | Time-aware interpretation |
| Ethnicity/genetics | Baseline differences in TGF-β, NO levels | Optional demographic feature |
| Ambient light contextual conditions | Affects spectral background | Device self-calibration and AI filtering |
| Device-to-device variance | Hardware inconsistencies | Embed probe-specific calibration metadata |

TABLE 26

| Systemic Integration Strategies for these Variables |
|---|

Metadata-Aware AI Models: Train models using input matrices that include age, sex, medication, comorbidities, etc.
Pre-classification Filter or Flag Layer: A logic layer before final diagnosis that adjusts or annotates predictions based on these factors.

TABLE 26-continued

Systemic Integration Strategies for these Variables

Bias Auditing & Fairness Checks: Ensure the model performs equally well across sex, age groups, and ethnic backgrounds.

TABLE 27

AI Flow Description: Context-Awareness Spectral Analysis Pipeline

The following flowchart stages define the AI system pipeline:
1. Spectral Input: Raman data is collected from the anterior chamber.
2. Contextual Metadata Entry: Patient data such as age, sex, diagnosis, and medication use is entered or retrieved.
3. Signal Preprocessing: Raman spectrum is normalized, denoised, and quality-checked.
4. Feature Augmentation: Contextual metadata is encoded as input vectors alongside spectral features.
5. Model Inference: A context-aware machine learning model evaluates biomarker signatures in the presence of relevant modifiers.
6. Confidence Calibration: A reliability score is computed based on signal quality and contextual complexity.
7. Output: Diagnostic category, confidence score, and annotation flags are presented to the user.

Figure 3:
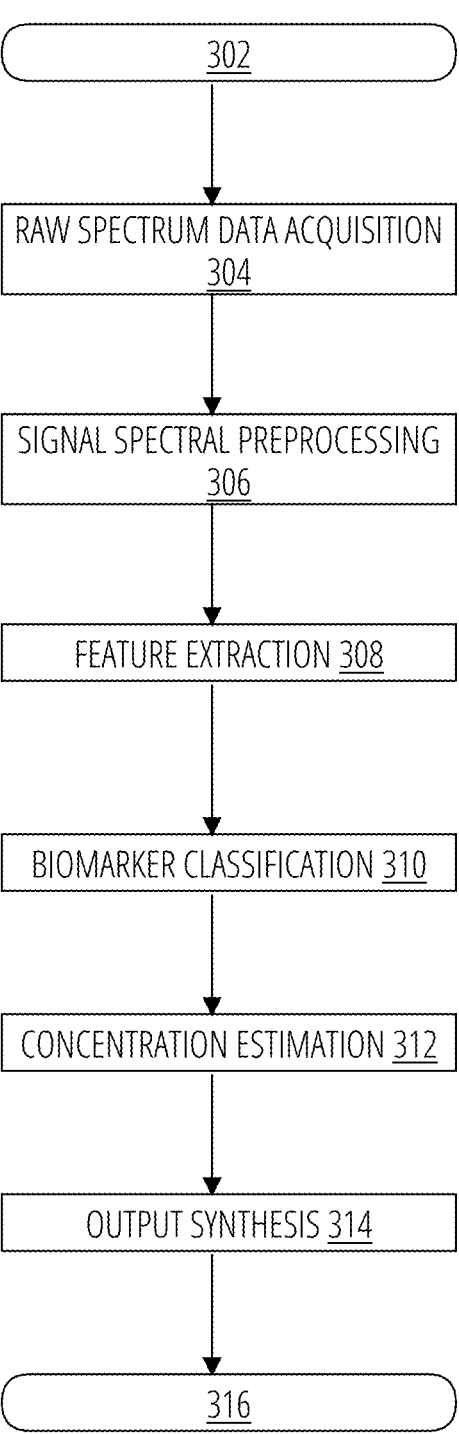
FIG. 3 is a flowchart of the AI workflow for spectral interpretation.

FIG. 3 is a flowchart of the AI workflow for spectral interpretation. The process starts with the start block 302. Then the raw spectrum data may be acquired, in block 304, from the spectrometer 116. Then, the spectrum data may be processed by the spectral data acquisition module 208 in block 306. This may include the subtraction of the fluorescence baseline and noise suppression using AI-trained autoencoders.

The features may then be extracted in block 308 by identifying the peaks and looking for the peaks associated with collagen, TGF-β2, and oxidative damage signatures. The biomarkers could then be classified using supervised machine learning (e.g., Support vector machines (SVM), convolutional neural networks (CNN)) to determine a disease indicated by the biomarkers.

Next, a concentration could be estimated in block 312 using quantitative analysis and AI regression. Finally, the output is synthesized into a risk score, a trend graph, and/or a comparative overlay. In some embodiments, this output is sent to the user interface 132. And the process reaches the done block 316.

This end-to-end AI pipeline enables molecular fingerprinting in a matter of seconds, supporting real-time diagnostics.

The disclosed AI-enhanced Raman spectroscopy diagnostic system 112 provides a non-invasive, AI-enhanced Raman spectroscopy diagnostic system 112 designed for the detection and quantification of molecular biomarkers and pharmacologic agents in the anterior chamber of the eye 102, with particular application to glaucoma diagnostics. See FIG. 3.

Raman spectral data may be collected, in block 304, using either the configuration in FIG. 1, a handheld probe, or a slit lamp-mounted configuration, with the excitation laser 106 source that may operate at 785 nm to deliver low-power pulses that conform to ANSI-defined ocular exposure limits. To ensure safe and precise acquisition, the AI-enhanced Raman spectroscopy diagnostic system 112 may incorporate real-time iris and corneal tracking, allowing for stable alignment throughout the scanning process.

Once the spectral data is acquired, the AI-enhanced Raman spectroscopy diagnostic system 112 may apply a robust signal preprocessing pipeline, as in block 306. Raw spectra undergo baseline subtraction and are corrected for cosmic ray spikes. Signal smoothing is achieved through Savitzky-Golay filters, and denoising autoencoders are deployed to eliminate fluorescence background, enabling the reconstruction of cleaner Raman signatures. To ensure comparability across samples, vector-based spectral normalization is applied, enhancing consistency for downstream analysis.

Following preprocessing, the AI-enhanced Raman spectroscopy diagnostic system 112 may extract latent spectral features, in 308, using advanced dimensionality reduction techniques such as principal component analysis (PCA), wavelet decomposition, or t-distributed stochastic neighbor embedding (t-SNE). Key Raman shifts associated with biomarkers—including but not limited to TGF-β2 (~1123 $cm^{-1}$), malondialdehyde (MDA, ~1470 $cm^{-1}$), and fibronectin—are isolated and fed into the artificial intelligence modeling framework.

The artificial intelligence engine 202 may be composed of a hybrid ensemble architecture, combining several model types tailored to different analytical objectives. Convolutional neural networks (CNNs) with residual learning layers are used to process full-spectrum 2D Raman intensity matrices for disease classification, while gradient-boosted regression trees handle biomarker quantification. Temporal dynamics in patient data are captured using long short-term memory (LSTM) models. Notably, the ensemble is designed with specific adaptations for glaucoma diagnosis.

To enhance diagnostic fidelity, spectral features are fused with clinical metadata, including intraocular pressure (IOP), optical coherence tomography (OCT) measurements, and demographic factors such as age, using a combination of concatenation and attention mechanisms. This multimodal fusion enables the AI-enhanced Raman spectroscopy diagnostic system 112 to dynamically weight input features and improve diagnostic performance as the AI-enhanced Raman spectroscopy diagnostic system 112 seeks to classify the biomarkers in block 310.

The AI/ML interpretation models 134 may be trained on a curated dataset comprising labeled Raman spectra from clinical aqueous humor samples with verified glaucoma status. To increase generalizability and mitigate overfitting, the training protocol incorporates data augmentation, synthetic interpolation, and class rebalancing strategies.

In some embodiments, the AI-enhanced Raman spectroscopy diagnostic system 112 estimates the concentration of various biomarkers in block 312.

For real-time deployment, the AI-enhanced Raman spectroscopy diagnostic system 112 may utilize TensorRT-optimized models, allowing for scan analysis of less than one second. Diagnostic results, including classification probabilities, biomarker concentration levels, and trend scores, may be displayed, in block 314, via an intuitive graphical interface. These results can be cross-referenced with imaging and clinical data such as OCT, fundus photography, and IOP measurements.

Explainability, using an explainability module 204, may be a component of the AI-enhanced Raman spectroscopy diagnostic system 112. Model outputs could be paired with interpretable visualizations, including Grad-CAM for CNNs and SHAP values for tree-based models, allowing clinicians to see which spectral regions contributed most significantly to the diagnostic outcome. The AI-enhanced Raman spectroscopy diagnostic system 112 may further incorporate a bias detection module that monitors algorithm performance across demographic subgroups and issues alerts in the event of drift or disparities.

The AI-enhanced Raman spectroscopy diagnostic system 112 may support data privacy and institutional autonomy through federated learning frameworks. This allows model updates to be trained on-device across multiple clinics without centralizing patient data. Diagnostic outputs can be accessed remotely via a secure cloud infrastructure, facilitating continuous model improvement and integration into distributed care environments.

This comprehensive, real-time Raman-AI framework offers an innovative, scalable solution for the molecular diagnosis of glaucoma and related ocular conditions, supporting both clinical decision-making and patient monitoring with unmatched precision and interpretability.

Figure 4:
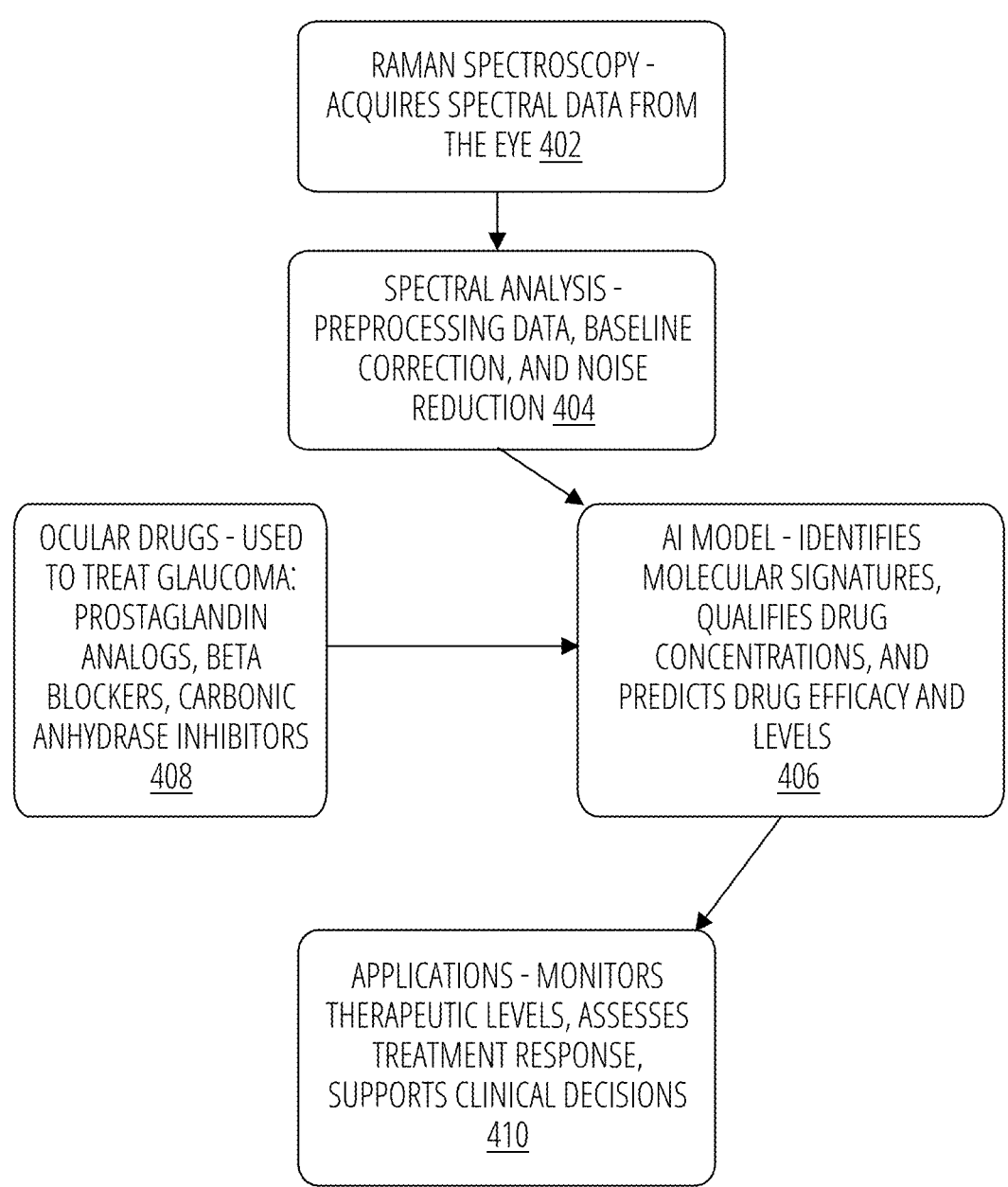
FIG. 4 is a flowchart showing one possible embodiment of the operation of the AI-enhanced Raman spectroscopy diagnostic system.

FIG. 4 is a flow chart of the evaluation of drug presence and concentrations, showing one possible embodiment. First, the Raman Spectroscopy—acquires spectral data from the eye 402. Then, a Spectral Analysis—preprocessing data, baseline correction, and noise reduction 404 may be performed to prepare the spectral data for AI processing. A list of Ocular Drugs—used to treat glaucoma: prostaglandin analogs, beta blockers, carbonic anhydrase inhibitors 408 along with the spectral data is sent to the AI Model—identifies molecular signatures, qualifies drug concentrations, and predicts drug efficacy and levels 406 for interpretation. These Applications—monitors therapeutic levels, assesses treatment response, supports clinical decisions 410.

Figure 5:
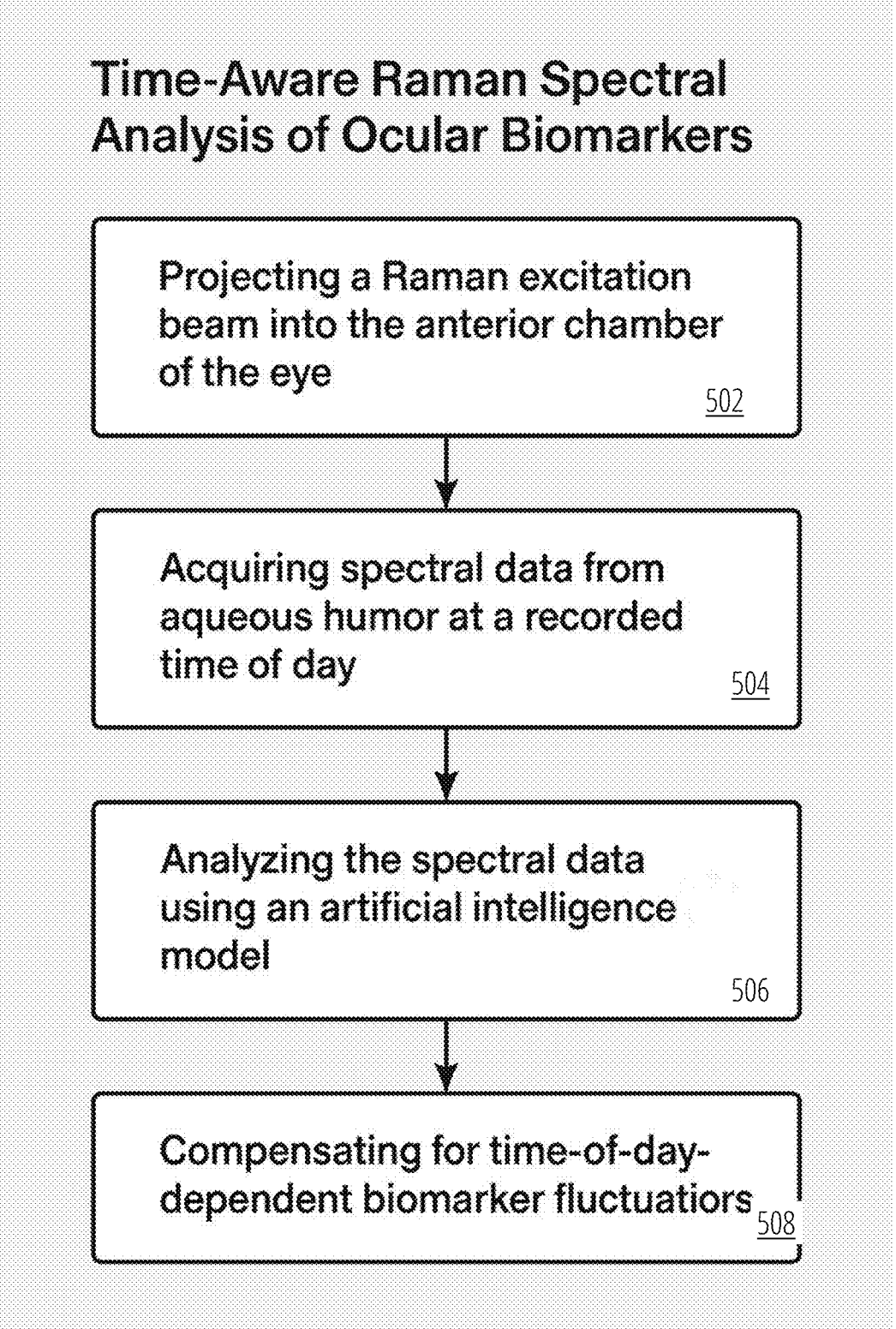
FIG. 5 is a flowchart showing another possible embodiment of the operation of the AI-enhanced Raman spectroscopy diagnostic system compensating for time-of-day fluctuations.

FIG. 5 is a flowchart of time-aware Raman spectral analysis of ocular biomarkers. The process begins by projecting a Raman excitation beam into the anterior chamber of the eye 502. From the reflection of the beam, the next step may involve acquiring spectral data from aqueous humor at a recorded time of day 504. Then, analyzing the spectral data using an artificial intelligence model 506, and finally compensating for time-of-day dependent biomarker fluctuation 508.

Figure 6:
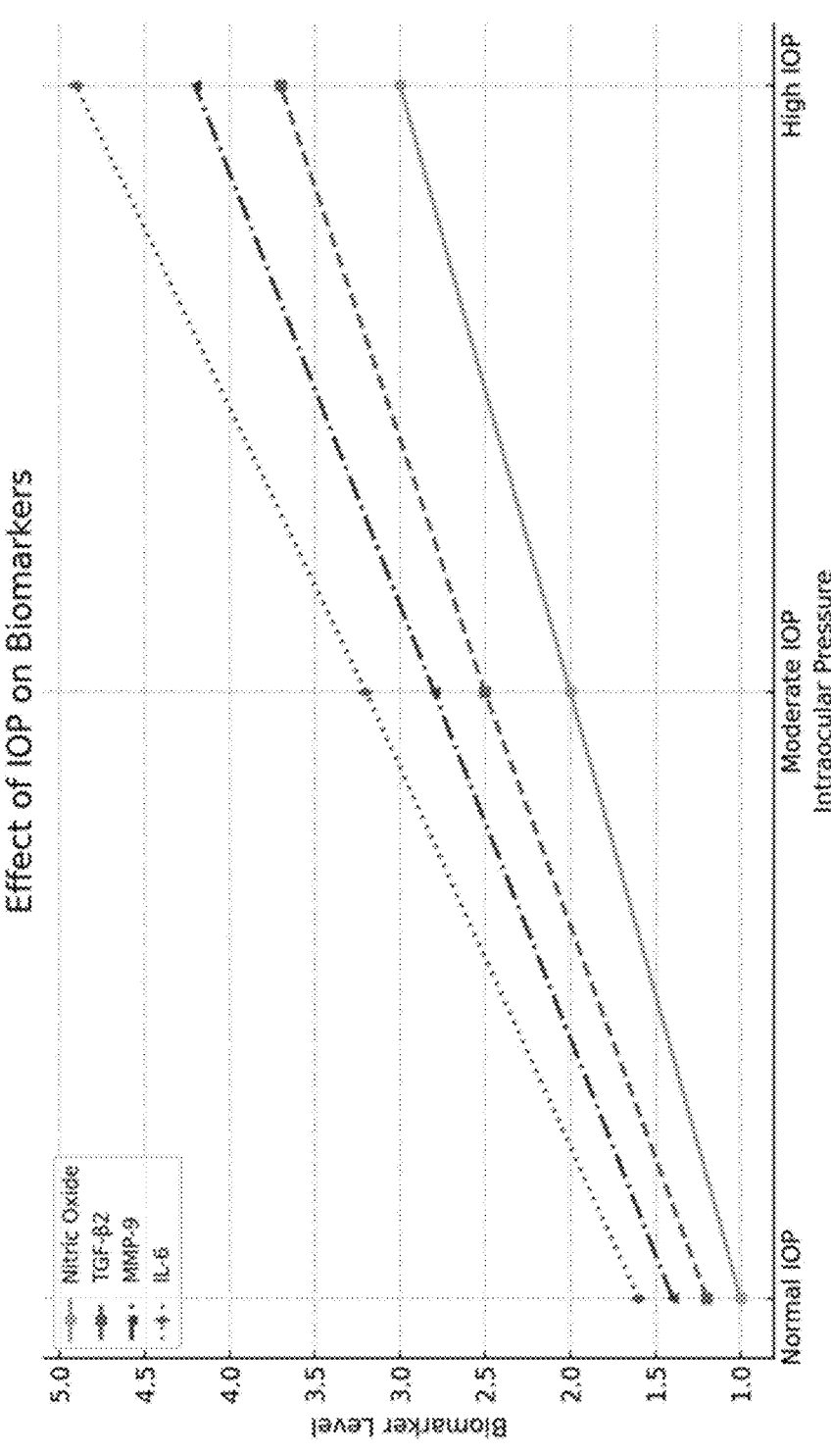
FIG. 6 shows the characteristic responses of various biomarkers to different intraocular pressure states.

FIG. 6 is a chart of the biomarker levels of Nitric Oxide, TGF-β2, MMP-9 and IL-6 as intraocular pressure increases from normal to a high level.

Figure 7:
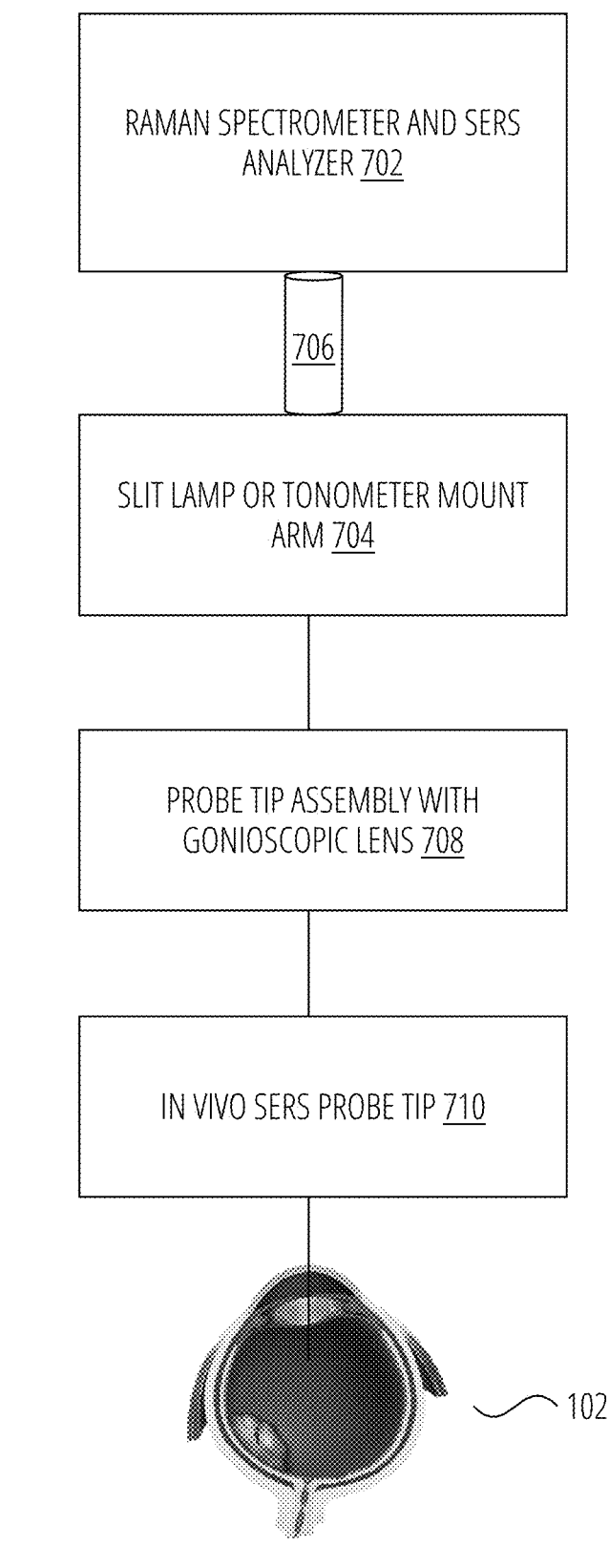
FIG. 7 illustrates a SERS embodiment of the AI-enhanced Raman spectroscopy diagnostic system.

In FIG. 7, a surface-enhancing substrates (SERS) embodiment is shown. In this embodiment, the Raman spectroscopy probe 142 in FIG. 1 is replaced with a SERS Raman probe 714. The SERS Raman probe 714 has a Raman spectrometer and SERS analyzer 702 that may be communicatively connected to the computer 118. The Raman spectrometer and SERS analyzer 702 may include a 785 nm laser and a SERS analyzer. The Raman spectrometer and SERS analyzer 702 may be connected through a fiber-optic cable 706 to a slit lamp or tonometer mount arm 704. The slit lamp or tonometer mount arm 704 is communicatively connected to a probe tip assembly with gonioscopic lens 708 (which may be a clear contact in some embodiments) which connects to the in vivo SERS Probe tip 710. The in vivo SERS Probe tip 710 may include a SERS-active substrate (e.g., gold-coated nanoarray), a transparent window aligned with the anterior chamber, and a Confocal Raman focus for spatial specificity. The in vivo SERS Probe tip 710 is in contact with the aqueous humor of the anterior chamber of the eye 102.

The SERS Raman probe 714 may use a biocompatible transparent window and/or gonioscopic lens for access. The SERS Raman probe 714 may include a confocal Raman alignment system for focused excitation. The SERS substrate may be embedded or positioned near the probe tip, optionally retractable. The SERS Raman probe 714 be can be slit lamp-mounted or tonometer-integrated for stable ophthalmic use.

In a clinical situation, the in vivo SERS Probe tip 710 contacts the corneal surface via gel or lens. The SERS-active region samples the aqueous humor 138 directly. The laser excites the molecules, the probe tip assembly with gonioscopic lens 708 observes the reflected laser beam, and the Raman signal is returned via the fiber-optic cable 706. AI-assisted spectral analysis in the artificial intelligence engine 202 may identify and quantify biomarkers observed in the aqueous humor 138.

The SERS Raman probe 714 uses a low-power near-infrared laser (785 nm) to avoid thermal damage. Biocompatible materials are used for any intraocular contact. Optionally, the SERS Raman probe 714 may use non-contact SERS substrates for enhanced safety.

Figure 8:
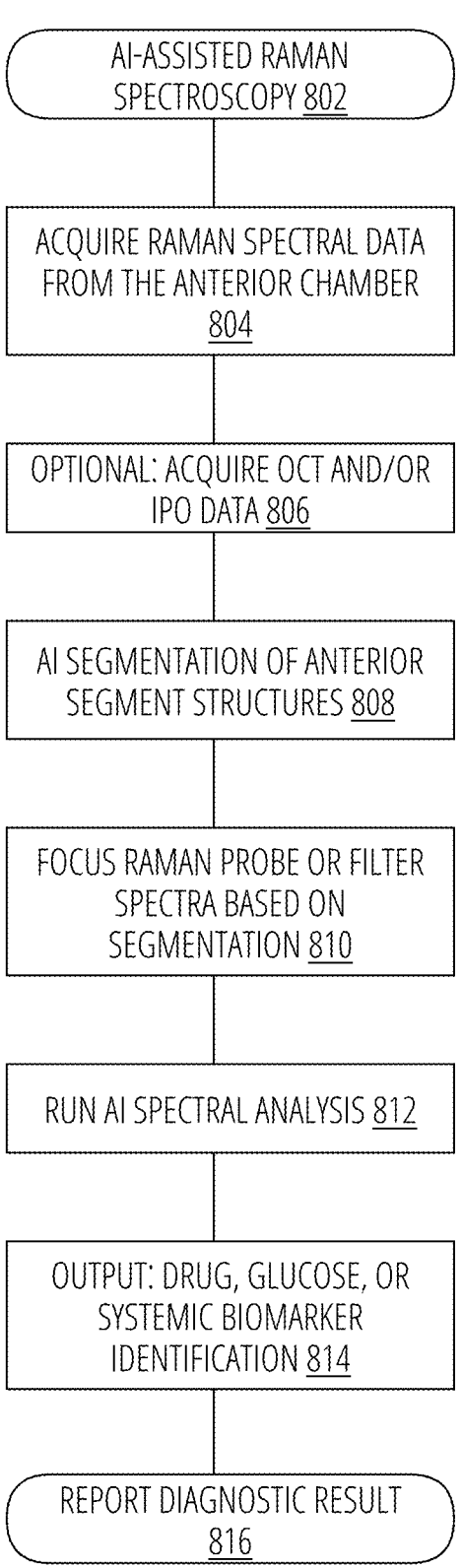
FIG. 8 is a flowchart illustrating the biomarker detection using segmentation in aqueous humor.

FIG. 8 is a flowchart of one embodiment of the AI-enhanced Raman spectroscopy diagnostic system 112 using segmentation to detect biomarkers. The start block 802 begins the process of using AI-assisted Raman Spectroscopy. First, the Raman spectral data is acquired from the aqueous humor 138 in the anterior chamber of the eye 102 in block 804. In some embodiments, ACT data is obtained from an Optical Coherence Tomography 136 in block 806. In some embodiments, the interocular pressure is obtained from other devices or from a medical record (block 806). Next, the segmentation engine 222 performs an AI segmentation of the anterior segment structures, such as Schlemm's canal, the trabecular meshwork, the cornea, etc., in block 808). This determines where to aim the focus of the Raman spectroscopy probe 142. The Raman spectroscopy probe 142 is then focused or filtered to retrieve data from a specific segment based on the segmentation in block 810. The artificial intelligence engine 202 then, runs the AI spectral analysis on the retrieved segmented data in block 812. The drug, glucose, or systemic biomarker identification is then assembled by the report generator 114 in block 814 and the diagnostic report may be displayed in the user interface 132 in the done block 816.

AI System Maintenance and Modular Updates

The disclosed AI-enhanced Raman spectroscopy diagnostic system 112 may be designed for long-term clinical utility through a modular, maintainable architecture that supports periodic updates and adaptive learning. In real-world applications, maintaining system accuracy and clinical relevance may require not only ongoing AI retraining but also careful coordination with updates in Raman spectroscopy hardware and signal acquisition protocols.

TABLE 28

AI System Maintenance and Modular Updates

1. Monitoring and Performance Evaluation
Continuously track AI model performance using diagnostic accuracy, confidence scores, and clinician feedback.
Identify drifts, anomalies, or degradations in diagnostic output.
↓
2. Trigger for Update
Detection of new biomarkers or Raman spectral shifts.
Discovery of new pharmaceutical agents or therapeutic regimes.
Changes in Raman hardware (e.g., new laser wavelength, resolution).
Updated clinical guidelines or diagnostic criteria.
Performance drop or user feedback suggesting recalibration.
↓
3. Modular Update Preparation
Isolate affected modules (e.g., biomarker recognition, spectral preprocessing, and pharmacologic interpretation).
Integrate new spectral data, metadata schemas, or Raman system parameters.
Apply augmentation, normalization, and synthetic training strategies to new data.
↓
4. Model Retraining and Validation
Fine-tune AI models using updated datasets.
Employ stratified validation, cross-clinic testing, and comparison against baseline models.
Update AI components in modular form without requiring full system replacement.
↓
5. Regulatory and Safety Checks
Perform validation checks aligned with clinical safety standards (e.g., ISO, FDA, and ANSI).
Document version history and model interpretability logs.
Verify compliance with privacy and federated learning standards.
↓
6. Deployment of Updated Modules
Push update to clinical systems via secure cloud or on-device update.
Maintain backward compatibility and optional rollback features.
Notify clinicians of update scope and relevance.
↓
7. Post-Deployment Monitoring
Collect post-update performance data in real time.
Solicit user feedback to verify usability, interpretability, and trust.
Log new data for future training cycles.

Ongoing Maintenance

Artificial intelligence models are not static; their performance can degrade over time due to changes in patient demographics, evolving clinical standards, or shifts in disease patterns. Additionally, the discovery of novel biomarkers, changes in drug usage patterns, or the emergence of new Raman-detectable substances all necessitate model updates.

The Raman spectroscopy subsystem itself may evolve. As hardware improves—through enhanced detectors (charge-coupled device 110), altered laser 106 parameters, or expanded spectral resolution—the characteristics of raw spectral data may shift. These changes can affect signal intensity, baseline behavior, or noise profiles, leading to subtle differences in the spectral inputs that the AI/ML interpretation model 134 must interpret. Without alignment, these hardware improvements may outpace the capabilities of pre-trained models, leading to decreased diagnostic reliability or misclassification.

Implementation of Modular Updates

Updates may include:

Clinical Integration: Updates are applied through secure interfaces, enabling both cloud-based and offline clinical environments to remain up-to-date.

Federated Learning Support: Allows decentralized training using anonymized local datasets while maintaining global model consistency.

Changelog Auditing: Each update is tracked with detailed release notes, model deltas, and performance comparisons.

By aligning AI/ML interpretation model 134 maintenance with Raman system upgrades, the disclosed diagnostic platform ensures that its molecular interpretation engine remains harmonized with signal acquisition capabilities. This coordinated approach enables the AI-enhanced Raman spectroscopy diagnostic system 112 to preserve accuracy, remain responsive to technological advances, and deliver actionable, real-time diagnostics with consistent reliability.

AI System Maintenance and Modular Updates

To maintain peak performance and clinical relevance, the AI-enhanced Raman spectroscopy diagnostic system 112 may be designed with modular update architecture. This allows for individual components—such as AI models (such as the models in the CNN classifier 128, the AI/ML interpretation model 134, the explainability module 204, the concentration estimation module 206, the biomarker classification module 210, the pharmacologic detection module 212, and the clinical protocol module 214), data inputs, user interfaces, and instrumentation protocols—to be independently maintained and upgraded over time without disrupting the entire system.

MODEL PERFORMANCE AND RETRAINING: As the AI-enhanced Raman spectroscopy diagnostic system 112 collects more real-world data, periodic retraining of AI models becomes useful to prevent model drift, improve generalizability, and accommodate new patient populations. These updates enhance diagnostic accuracy and expand the applicability of the artificial intelligence engine 202 across diverse clinical settings. Modular updates enable the seamless integration of updated neural network weights, new feature extraction methods, or improved interpretive logic, all without requiring a complete AI-enhanced Raman spectroscopy diagnostic system 112 overhaul.

CLINICAL DATASET EXPANSION: Over time, additional biomarker data may emerge from clinical research or multi-center collaborations. These datasets may include new disease presentations, racial or ethnic subpopulations, and biomarker variability due to environmental or pharmacologic exposures. The modular structure allows these data to be imported for retraining or for supervised fine-tuning, ensuring that the AI-enhanced Raman spectroscopy diagnostic system 112 continues to reflect evolving clinical realities.

INTEGRATION OF NEW BIOMARKERS: As novel biomarkers are identified—whether proteins, cytokines, metabolites, or vesicle-bound signals—the artificial intelligence engine 202 can be updated with new spectral templates and diagnostic classifications. Each new biomarker module includes its unique Raman spectral signature, interpretive thresholds, and clinical context (e.g., early glaucoma vs. inflammatory response). This dynamic integration expands diagnostic scope without altering existing validated functions.

PHARMACOLOGIC DETECTION UPDATES: The AI-enhanced Raman spectroscopy diagnostic system 112 is also engineered to detect therapeutic agents in the aqueous humor 138, such as prostaglandin analogs, corticosteroids, and investigational drugs. As new compounds are introduced into clinical practice, corresponding modules can be added to the artificial intelligence engine 202 to recognize their Raman features and estimate concentrations. These pharmacologic updates refine treatment monitoring and compliance analysis.

CHANGES IN CLINICAL PROTOCOLS: The modular design ensures adaptability when clinical practice patterns change, whether in response to revised diagnostic criteria, new treatment guidelines, or evolving screening protocols. Updates to decision thresholds, interpretive logic, or user prompts can be delivered as independent software modules without necessitating hardware changes or model retraining.

HARDWARE OR SOFTWARE INFRASTRUCTURE ENHANCEMENTS: If the Raman spectrometer 116r undergoes hardware updates, such as changes in laser 106 wavelength, detector (charge-coupled device 110) sensitivity, or optical resolution, the artificial intelligence engine 202 is configured to accommodate new signal characteristics. Signal preprocessing modules and spectral normalization layers (spectral data acquisition module 208) can be adjusted or replaced as plug-in components to match the updated hardware profile. Similarly, updates in the user interface 132 or data storage 122 architecture are handled modularly to preserve workflow stability.

COORDINATION WITH RAMAN SPECTROSCOPY IMPROVEMENTS: As Raman instrumentation improves, introducing better signal-to-noise ratios, enhanced optical filtering, or new excitation protocols, the AI-enhanced Raman spectroscopy diagnostic system 112 may require concurrent updates to maintain interpretive accuracy. These include recalibration of signal preprocessing algorithms, normalization protocols, and spectral resolution parameters.

The modular framework ensures that the AI adapts in parallel with advancements in the AI-enhanced Raman spectroscopy diagnostic system 112.

SECURITY AND COMPLIANCE UPDATES: Finally, as privacy laws and clinical data standards evolve (e.g., GDPR, HIPAA, FDA guidance), the modular design allows updates to be delivered to the security, logging, and audit modules 218. These changes enhance compliance without affecting diagnostic performance.

The invention claimed is:

1. A system comprising:
   a Raman spectroscopy assembly including:
      a laser excitation source configured to direct a laser beam at aqueous humor in an eye; and
      a charge coupled device configured to receive light from the laser beam reflected from the aqueous humor in the eye and generate signals based on the light;
   a computer, communicatively connected to the Raman spectroscopy assembly, including:
      a spectral data acquisition module that reads the signals from the charge coupled device and produces a Raman spectra;
      a stacked autoencoder, trained on reference aqueous humor Raman spectra, that denoises the Raman spectra into a processed Raman spectra;
      an artificial intelligence engine, trained on the reference aqueous humor Raman spectra, where the reference aqueous humor Raman spectra includes the reference aqueous humor Raman spectra for a transforming growth factor-beta 2 (TGF-β2) biomarker, to compare disease-associated spectral patterns in the processed Raman spectra using a convolutional neural network classifier, where the convolutional neural network classifier outputs biomarkers relevant to the disease-associated spectral patterns; and
      a concentration estimation module that estimates a magnitude of the biomarkers in the processed Raman spectra into biomarker concentrations using regression models that correlate peak intensities in the processed Raman spectra; and
   a user interface, communicatively connected to the computer, configured to display the biomarkers and the biomarker concentrations.

2. The system of claim 1, wherein the Raman spectroscopy assembly is configured to be integrated with a slit lamp.

3. The system of claim 1, further comprising a graphical user interface configured to visualize diagnostic results, biomarker trends, and disease risk scores.

4. The system of claim 1, wherein the artificial intelligence engine includes autoencoders configured to perform baseline correction and noise filtering.

5. The system of claim 1, wherein the artificial intelligence engine integrates Raman spectral data with one or more physiological, anatomical, or imaging-based data sources, including at least one of: optical coherence tomography (OCT) data, intraocular pressure (IOP) measurements, biometric imaging, or systemic clinical data.

6. The system of claim 1, wherein the biomarkers include MMPs, TIMPs, fibronectin, or oxidative stress markers.

7. The system of claim 1, configured for longitudinal monitoring of disease progression.

8. The system of claim 1, further comprising a safety subsystem that regulates an output of the laser excitation source to conform to ANSI Z136.1 ocular exposure limits.

9. The system of claim 8, wherein the safety subsystem monitors and limits a duration and intensity of exposure to the laser excitation source based on prognosis.

10. The system of claim 8, wherein said safety subsystem includes a laser modulation circuit connected to the laser excitation source and timed pulse delivery mechanism.

11. The system of claim 10, wherein the laser excitation source operates at 785 nm±5 nm to optimize Raman signal quality and ocular safety.

12. The system of claim 1, wherein the laser excitation source operates in pulsed or time-gated mode to reduce cumulative energy exposure to ocular tissues.

13. The system of claim 1, wherein the Raman spectroscopy assembly includes optical safety sensors and alignment tracking configured to ensure safe operation during anterior chamber measurement.

14. The system of claim 1, wherein the artificial intelligence engine includes an explainability module configured to highlight spectral features contributing to classification decisions.

15. The system of claim 1, wherein the artificial intelligence engine is trained using federated learning across distributed clinical sites and is adaptable to include newly discovered biomarkers.

16. The system of claim 1, wherein the Raman spectroscopy assembly comprises surface-enhanced Raman spectroscopy (SERS) capability and is operable with or without confocal optical elements.

17. The system of claim 1, wherein the system is configured to capture spectral data in a range of 400 to 1800 cm$^{-1}$.

18. The system of claim 1, wherein Raman spectra acquisition includes temporal averaging of multiple spectra to increase signal-to-noise ratio under clinical lighting conditions.

19. The system of claim 1, wherein the artificial intelligence engine is trained to identify spectral biomarkers specific to glaucomatous changes in a trabecular meshwork.

20. The system of claim 1, wherein the artificial intelligence engine is configured to incorporate newly identified spectral biomarkers based on training from updated clinical databases.

21. The system of claim 1, wherein the artificial intelligence engine is configured to incorporate newly identified spectral biomarkers based on training from user-validated input.

22. The system of claim 1, wherein the laser excitation source emits laser energy at a power and divergence classified as Class 1M or Class 3R under ANSI Z136.1, ensuring maximum permissible exposure is not exceeded during use on a human eye.

23. The system of claim 1, wherein the artificial intelligence engine is trained on spectra from normal aqueous humor and aqueous humor with ocular diseases.

24. The system of claim 1, wherein the artificial intelligence engine is trained on spectra from normal aqueous humor and aqueous humor with drug-specific Raman peaks.

25. The system of claim 1, wherein the artificial intelligence engine is trained on spectra from normal aqueous humor and aqueous humor with verified glaucoma status.

26. The system of claim 1, where the biomarkers include newly discovered biomarkers.

* * * * *